US010524734B2

(12) United States Patent
Korzinov et al.

(10) Patent No.: US 10,524,734 B2
(45) Date of Patent: Jan. 7, 2020

(54) METHOD AND SYSTEM FOR MEASURING BEAT PARAMETERS

(71) Applicant: MAD Apparel, Inc., Redwood City, CA (US)

(72) Inventors: Lev Korzinov, Redwood City, CA (US); Ankit Gordhandas, Redwood City, CA (US); Christopher Wiebe, Redwood City, CA (US)

(73) Assignee: MAD Apparel, Inc., Redwood City, CA (US)

( * ) Notice: Subject to any disclaimer, the term of this patent is extended or adjusted under 35 U.S.C. 154(b) by 52 days.

(21) Appl. No.: 14/878,831

(22) Filed: Oct. 8, 2015

(65) Prior Publication Data
US 2016/0100803 A1 Apr. 14, 2016

Related U.S. Application Data

(60) Provisional application No. 62/061,261, filed on Oct. 8, 2014.

(51) Int. Cl.
A61B 5/00 (2006.01)
A61B 5/04 (2006.01)
(Continued)

(52) U.S. Cl.
CPC .......... A61B 5/7203 (2013.01); A61B 5/0402 (2013.01); A61B 5/04012 (2013.01);
(Continued)

(58) Field of Classification Search
CPC .. G06F 19/3406; G06N 99/005; G06N 5/022; G16H 40/63; A61B 5/7203;
(Continued)

(56) References Cited

U.S. PATENT DOCUMENTS 4,188,610 A * 2/1980 Nelson ............... G01V 1/04
367/14
5,776,070 A * 7/1998 Kitazawa ......... A61B 5/02422
600/483
(Continued)

FOREIGN PATENT DOCUMENTS

CN 1034609 A 8/1989

OTHER PUBLICATIONS

PCT International Search Report, PCT Application No. PCT/US15/54750, dated Jan. 5, 2016, 9 pages.

Primary Examiner — Lynsey C Eiseman
Assistant Examiner — Jessandra F Hough
(74) Attorney, Agent, or Firm — Fenwick & West LLP

(57) ABSTRACT

A method for communicating beat parameters to a user includes: providing an electrode module comprising a first and a second set of electrodes, associated with a first and a second sensor channel, respectively; receiving a first and a second dataset based on a first and a second set of bioelectrical signals detected from the first and the second sensor channel, respectively; receiving a supplemental dataset based on supplemental bioelectrical signals detected from a supplemental sensor module; generating a noise-mitigated power spectrum upon: generating a combined dataset based upon combining the first and second datasets, calculating 1) a heart power spectrum based on the combined data set, and 2) a supplemental power spectrum based on the supplemental dataset, and generating a noise-mitigated power spectrum based on processing the heart power spectrum with the supplemental power spectrum; and rendering information derived from a beat parameter analysis to the user.

22 Claims, 14 Drawing Sheets

(51) Int. Cl.
*A61B 5/0402* (2006.01)
*A61B 5/0488* (2006.01)
*G06N 5/02* (2006.01)
*G16H 40/63* (2018.01)
*A61B 5/0472* (2006.01)

(52) U.S. Cl.
CPC .......... *A61B 5/0488* (2013.01); *A61B 5/6804* (2013.01); *G06N 5/022* (2013.01); *A61B 5/0472* (2013.01); *A61B 5/746* (2013.01); *A61B 5/7475* (2013.01); *A61B 2562/04* (2013.01); *G16H 40/63* (2018.01)

(58) Field of Classification Search
CPC . A61B 5/04012; A61B 5/0402; A61B 5/0488; A61B 5/6804; A61B 5/7207; A61B 5/7221; A61B 5/0002; A61B 5/02405; A61B 5/0472; A61B 5/7275; A61B 5/746; A61B 5/7475; A61B 2562/04; A61B 5/0245; A61B 5/04014
See application file for complete search history.

(56) References Cited

U.S. PATENT DOCUMENTS

| | | | |
|---|---|---|---|
| 5,794,623 A | | 8/1998 | Forbes |
| 6,161,042 A | * | 12/2000 | Hartley .............. A61N 1/36521 600/547 |
| 6,930,608 B2 | | 8/2005 | Grajales et al. |
| 7,647,185 B2 | * | 1/2010 | Tarassenko .......... A61B 5/0245 702/19 |
| 7,689,275 B2 | * | 3/2010 | Blomberg .......... A61B 5/04004 128/203.14 |
| 7,797,039 B2 | * | 9/2010 | Koivumaa ........... A61B 5/0408 128/901 |
| 2006/0089557 A1 | | 4/2006 | Grajales et al. |
| 2006/0173370 A1 | | 8/2006 | Koivumaa et al. |
| 2007/0055151 A1 | * | 3/2007 | Shertukde .......... A61B 5/02007 600/437 |
| 2008/0033494 A1 | * | 2/2008 | Swerdlow .............. A61B 5/046 607/5 |
| 2008/0045815 A1 | | 2/2008 | Derchak et al. |
| 2009/0306485 A1 | | 12/2009 | Bell |
| 2010/0179447 A1 | | 7/2010 | Hunt |
| 2011/0152695 A1 | * | 6/2011 | Granqvist ............ A61B 5/0006 600/481 |
| 2012/0123232 A1 | * | 5/2012 | Najarian .............. A61B 5/0022 600/345 |
| 2014/0005988 A1 | * | 1/2014 | Brockway .......... H03H 17/0248 703/2 |
| 2014/0094707 A1 | | 4/2014 | Farringdon et al. |
| 2014/0107493 A1 | | 4/2014 | Yuen et al. |
| 2014/0135593 A1 | | 5/2014 | Jayalth et al. |
| 2016/0113587 A1 | * | 4/2016 | Kothe .................. A61B 5/7203 600/301 |

\* cited by examiner

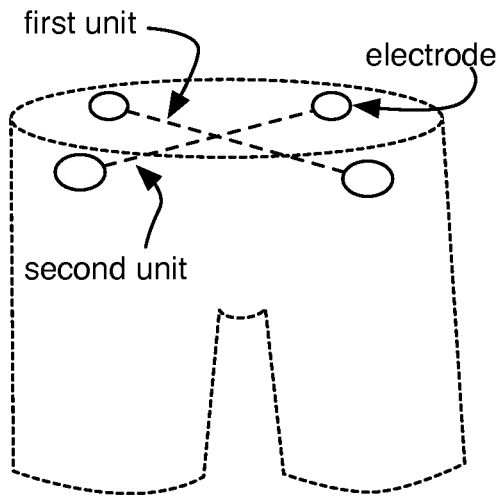
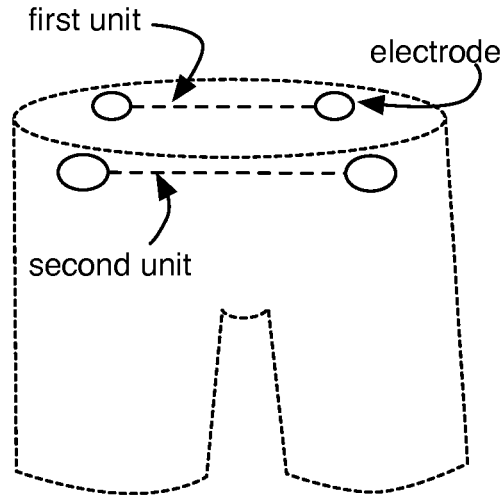
FIGURE 2A                FIGURE 2B
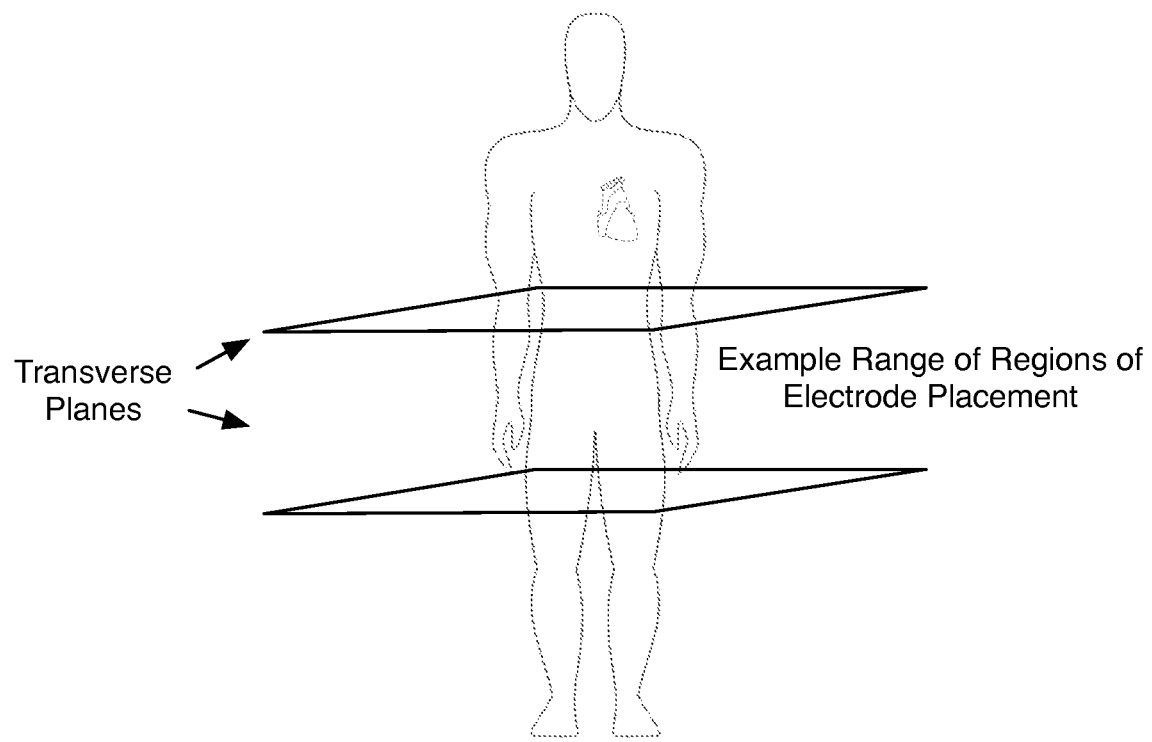
FIGURE 2C

METHOD AND SYSTEM FOR MEASURING BEAT PARAMETERS

CROSS-REFERENCE TO RELATED APPLICATIONS

This application claims the benefit of U.S. Provisional Application Ser. No. 62/061,261, filed on 8 Oct. 2014, which is incorporated herein in its entirety by this reference.

TECHNICAL FIELD

This invention relates generally to the biometric device field, and more specifically to a new and useful method and system for measuring beat parameters.

BACKGROUND

Conventional biometric monitoring devices often include electrical contacts that are placed in contact with skin of a user and monitor a bioelectrical signal using the electrical contacts. However, coupling of the electrical contacts to the user (e.g., using adhesives or straps) can not only constrain motion of the user, but can produce noise in response to any motions of the user. Furthermore, motion in conventional devices can result in interference and/or interruptions of a signal, contributing to periods wherein extracting information from received signals is difficult or near-impossible. In particular, extraction of an Electrocardiograph (ECG) parameter (e.g., beat parameter, heart rate parameter, R-R interval parameter) from signals generated by a biometric monitoring device is problematic when the user is in motion and/or signals are acquired from a position far from the heart of the user. Other limitations of conventional biometric monitoring devices include one or more of: involvement of single-use electrodes, involvement of a single set of electrodes targeting a single body location, use of adhesives for electrode placement, contributions to user discomfort, and other deficiencies.

There is thus a need in the biometric device field to create a new and useful method and system for measuring heart beat parameters. This invention provides such a new and useful method and system.

BRIEF DESCRIPTION OF THE FIGURES

FIGS. 2A, 2B and 2C depict variations of electrode unit configurations and positioning in an embodiment of a method and system for communicating beat parameters to a user at a user interface of an electronic device associated with the user;

DESCRIPTION OF THE PREFERRED EMBODIMENTS

The following description of the preferred embodiments of the invention is not intended to limit the invention to these preferred embodiments, but rather to enable any person skilled in the art to make and use this invention.

1. Method

Figure 1:
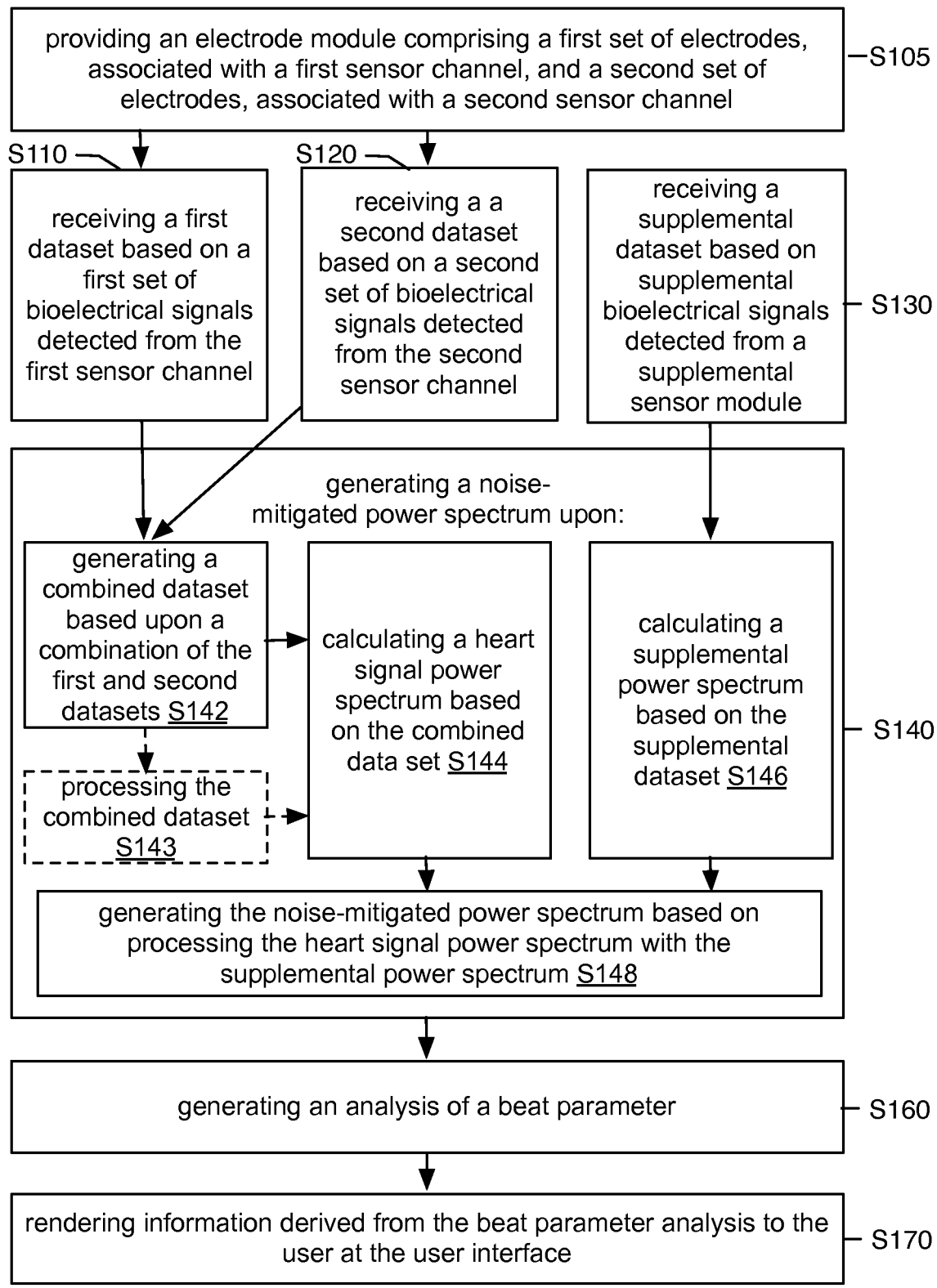
FIG. 1 depicts an embodiment of a method for communicating beat parameters to a user at a user interface of an electronic device associated with the user.

As shown in FIG. 1, an embodiment of a method 100 for communicating beat parameters to a user at a user interface of an electronic device associated with the user includes: providing an electrode module comprising a first set of electrodes, associated with a first sensor channel, and a second set of electrodes, associated with a second sensor channel S105; receiving a first dataset based on a first set of bioelectrical signals detected from the first sensor channel S110; receiving a second dataset based on a second set of bioelectrical signals detected from the second sensor channel S120, wherein the first dataset and the second dataset comprise a local noise component and a heart signal component; receiving a supplemental dataset based on supplemental bioelectrical signals detected from a supplemental sensor module S130; generating a noise-mitigated power spectrum S140 upon: generating a combined dataset based upon a combination of the first dataset and the second dataset S142, calculating 1) a heart signal power spectrum based on the combined data set S144, and 2) a supplemental power spectrum based on the supplemental dataset S146, and generating a noise-mitigated power spectrum based on processing the heart signal power spectrum with the supplemental power spectrum S148; generating an analysis of a beat parameter S160; and rendering information derived from the beat parameter analysis to the user at the user interface S170.

The method 100 functions to enable extraction of a beat parameter (e.g., heart rate parameter, R-R parameter) based upon processing multiple sensor channels of a sensor module in a manner that removes local noise effects resulting from placement of electrodes of the sensor module. In a specific example, the method 100 enables extraction of heart beat parameters from a user in near real-time, from multiple electrode channels of electrodes placed at or below the waistline of the user, while the user is performing a physical activity (e.g., exercising, weight lifting, etc.). The method 100 in this specific example then processes signals derived from the multiple electrode channels to mitigate local noise effects in extracting the heart beat parameters, based upon a processing algorithm that separates local noise from a signal from which the heart beat parameter can be derived. As such, the method 100 can take advantage of a strong correlation between distant source heart signals (e.g., from electrocardiography), in relation to a weak correlation between the distant source heart signals and local noise sources, as well as weak correlation between local noise sources of the independent sensor channels. The method 100 can, however, be configured to determine values of any other suitable cardiovascular parameter, for a user who is performing any other suitable activity. In some variations, the method 100 can be implemented for electrode systems integrated into garments (e.g., shorts, pants, tops, accessories (e.g., belts)) of the user, wherein the electrode systems can be removably integrated and/or configured for wireless communication of signals. As such, the method 100 can be implemented, at least in part, using an embodiment, variation, or example of system components described in U.S. application Ser. No. 14/541,446, entitled "System and Method for Monitoring Biometric Signals" and filed on 14 Nov. 2014, U.S. application Ser. No. 14/079,629, entitled "Wearable Architecture and Methods for Performance Monitoring, Analysis, and Feedback" and filed on 13 Nov. 2013, U.S. application Ser. No. 14/079,621, entitled "Wearable Performance Monitoring, Analysis, and Feedback Systems and Methods" and filed on 30 Jan. 2014, U.S. application Ser. No. 14/699,730, entitled "Biometric Electrode System and Method of Manufacture" and filed on 29 Apr. 2015, and U.S. application Ser. No. 14/742,420, entitled "Biometric Signal Conduction System and Method of Manufacture" and filed on 17 Jun. 2015, each of which is incorporated herein in its entirety by this reference.

However, the method 100 can additionally or alternatively be implemented using electrode systems that are not configured to be integrated into garments or accessories. As such, the method 100 is preferably implemented at an embodiment of the system 200 described in Section 2 below; however, the method 100 can alternatively be implemented using any other suitable system(s).

1.1 Method—Providing an Electrode Module

Block S105 recites: providing an electrode module comprising a first set of electrodes, associated with a first sensor channel, and a second set of electrodes, associated with a second sensor channel S105. Each of the first sensor channel and the second sensor channel preferably corresponds to a first unit of an electrode module (e.g., sensor module) and a second unit of the electrode module, respectively, wherein each unit includes a pair of electrodes. As such, signals transmitted through each of the first sensor channel and the second sensor channel are preferably derived from a consolidation of two electrode signals (e.g., a difference of two electrode signals); however, in alternative variations of Block S105, each unit corresponding to a sensor channel can include any suitable number of electrodes. In variations of a unit involving a pair of electrodes, the pair of electrodes is preferably positioned such that the electrodes oppose each other within the same plane (e.g., transverse plane) of the user's body. As such, a first vector (or projection thereof onto a plane) between electrodes of a first unit and a second vector (or projection thereof onto the plane) between electrodes of a second unit can cross, as shown in FIG. 2A, or may not cross, as shown in FIG. 2B. The example configuration shown in FIG. 2A can increase the amplitude of the coupled bioelectric signal generated by a pair of electrodes, wherein amplitude is increased by increasing the separation distance of the pair of electrodes across the body.

In providing the electrode module in Block S105, all electrodes of units corresponding to the first and the second channels preferably lie substantially within the same plane (e.g., a transverse plane through the user's body), such that vectors between the electrodes and a reference point (e.g., the user's heart) are approximately equal in magnitude. Such a configuration produces a high degree of correspondence (i.e., phase alignment) between signals generated at the electrodes of the units. In variations, as shown in FIG. 2C, the plane can be a transverse plane through the user's body, at or below the umbilical region of the user (to provide a suitable distance from the heart of the user, in relation to signal timing) and at or above a plane through the greater trochanter bones of the user's femurs (in order to limit noise due to motion of the user). In one example, all electrodes can be positioned about the waistline of a garment (e.g., pants, shorts) of the user. Alternatively, electrodes of different units corresponding to the sensor channels can lie within different planes (e.g., slightly offset planes), such that differences in magnitudes between vectors from the electrodes to a reference point (e.g., the user's heart) are negligible. Even further, all electrodes of units corresponding to sensor channels can be positioned such that they receive signals generated from the user's heart or any other suitable reference point with substantially the same timing. As such, suitable distance between the heart of the user and electrodes can facilitate reception of substantially in-phase signals from a distant heart source, while local noise in signals from each sensor channel remain substantially uncorrelated. However, electrodes of units corresponding to the sensor channels can alternatively be positioned at any other suitable location, and subsequent blocks of the method 100 can be configured to account for distance and/or asymmetry in electrode configuration in extracting beat parameters from the datasets.

In some variations, Block S105 can include providing a conductive medium (e.g., electrolyte gel, etc.) configured between electrical contacts and the body region(s) of the user, which functions to enhance coupling (e.g., physical, electrical) between the user and the electrode module in facilitating signal transmission through the first sensor channel and the second sensor channel. However, variations of Block S105 can alternatively be performed using any other suitable electrode, as described in Section 2 below.

Figure 3A:
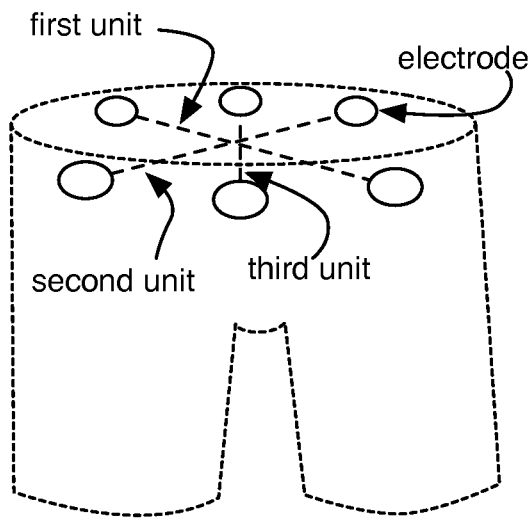
FIGS. 3A and 3B depict alternative sensor module configurations in an embodiment of a method and system for communicating beat parameters to a user at a user interface of an electronic device associated with the user.

While two sensor channels, each corresponding to a unit of two electrodes, are described above, variations of the method 100 can be expanded to receive less than or more than two sensor channels (e.g., N sensor channels). For instance, in some variations, three sensor channels, each having a unit of two electrodes, can be used to generate three datasets in a manner analogous to that of Blocks S110 and S120. In an example, as shown in FIG. 3A, electrodes of each unit can be positioned about the user's waistline and be located substantially within the same transverse plane through the user's body, in order to generate data which can be processed to identify beat parameters of the user.

1.2 Method—Receiving First, Second, and Supplemental Datasets

Block S110 recites: receiving a first dataset based on a first set of bioelectrical signals detected from the first sensor channel S110; Block S120 recites: receiving a second dataset based on a second set of bioelectrical signals detected from the second sensor channel S120; and Block S130 recites receiving a supplemental dataset based on supplemental bioelectrical signals detected from a supplemental sensor module S130. Blocks S110 and S120 function to receive multiple channels of bioelectrical signals from a user, which can be simultaneously processed to isolate and separate noise (e.g., locally-induced noise) from signals of interest. As such, the first dataset and the second dataset can be expected to include a signal component from the heart of the user (i.e., a heart beat signal) and a local noise component, which can be isolated and separated in subsequent blocks of the method 100 in order to derive at least one beat parameter of the user. Block S130 functions to receive a supplemental dataset that can be processed for use in facilitating the isolation and separation of noise (e.g. locally-induced noise) from the signals of interest.

In Blocks S110, S120, and S130, the first dataset, the second dataset, and the supplemental dataset are preferably received at a processing subsystem, as described in Section 2 below, wherein the processing subsystem can be implemented in one or more of: a hardware processing subsystem, a cloud-based processing subsystem, and any other suitable processing subsystem. Blocks S110, S120, and S130 preferably include receiving datasets, at the processing subsystem, derived from electrical contacts (i.e., biometric electrodes) configured to electrically couple to a body region of the user, in order to enable bioelectrical signal transmission from the user through the contacts. The first, the second, and the supplemental dataset are preferably received from a communication subsystem, as described in Section 2 below, that transmits the datasets to the processing subsystem upon receiving the datasets from the sensor channels. Alternatively, the first, the second, and the supplemental dataset can be received from the first, second, and supplemental sensor channel, respectively. However, the datasets can be received at any suitable component, from any suitable component, and in any suitable manner.

In some variations, Blocks S110, S120, and S130 can include generating a first conditioned dataset, a second conditioned dataset, and a supplemental conditioned dataset based upon processing the first, the second, and the supplemental datasets at a filtering module S135, which functions to preprocess the datasets to remove frequencies resulting from known noise contributors. Block S135 preferably includes passing each of the first dataset, the second dataset, the supplemental dataset, and any other dataset (e.g., from an additional sensor channel) generated in Blocks S110, S120, and S130 through at least one of a low pass filter, a high pass, filter, a band-pass filter, and a notch filter (i.e., a band-stop filter), in order to preprocess the datasets to remove a portion of any artifacts or interference (e.g., due to noise). In variations, the low pass filter can function to remove higher frequency noise and the high pass filter can function to remove lower frequency noise (e.g., due to waist movement/pressure artifacts). Any of the filters can further be supplemented with filters configured to remove or mitigate the frequency spectrum of any known noise components. In a specific example, Block S135 includes passing each of the datasets through a low pass filter, a high pass filter, and a notch filter. The notch filter is used to filter out the mains hum resulting from power transmission coupling to the body of the subject and therefore coupling to the electrode module. However, different combinations of filters can be used to process different datasets.

Figure 4:
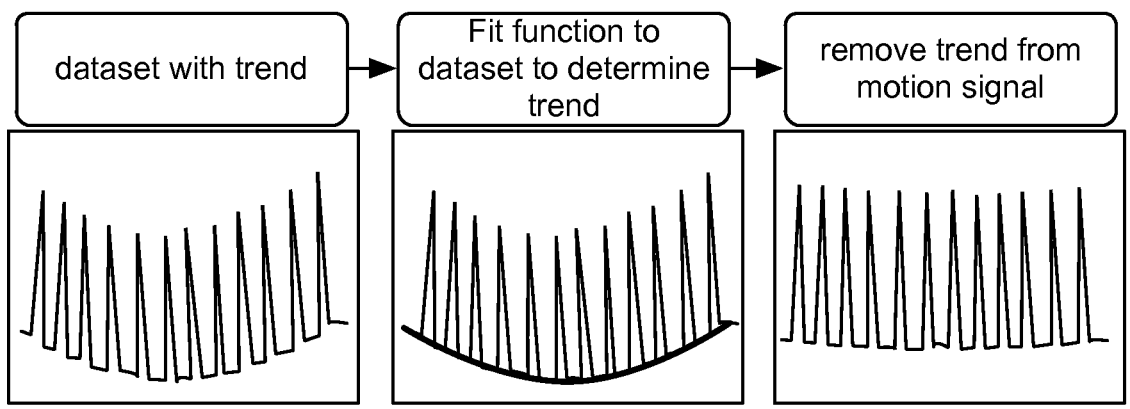
FIG. 4 depicts a variation of signal conditioning in an embodiment of a method for communicating beat parameters to a user at a user interface of an electronic device associated with the user.
Figure 5A:
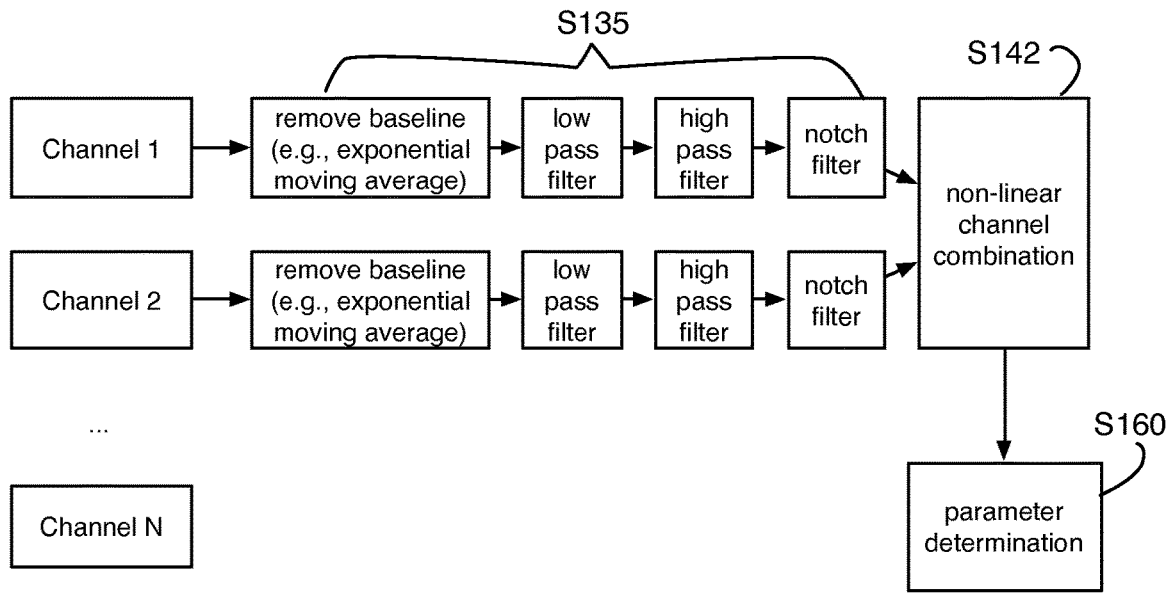
FIGS. 5A and 5B depict example signal conditioning flows for measuring beat parameters of a user from a first and second electrode unit.

Additionally or alternatively, to process the first dataset, the second dataset, the supplemental dataset, and any other dataset at the filtering module, Block S135 can include processing the datasets at a conditioning module configured to perform other suitable conditioning processes on the datasets. In variations, processing at the conditioning module can include any one or more of: smoothing, clipping, deconvolving, detrending/offsetting, standardizing, resampling, hard-binding, predicting, windowing, and performing any other suitable data conditioning process upon any data received in Blocks S110, S120, and S130. For instance, Block S135 can include processing a signal at a module configured to remove a baseline mean in a signal (e.g., based upon an exponential moving average), as shown in FIG. 5A. Additionally or alternatively, Block S135 can include removing a trend in at least one of the first dataset, the second dataset, and the supplemental dataset due to potential offsets between the first and second electrode of the sensor module and/or gross motion (e.g., moving from a sitting to a standing position) of the user, which can include fitting a trend function to the trend of a dataset, and subtracting the trend function from the dataset to detrend the dataset, as shown in FIG. 4. As such, Block S135 outputs conditioned versions of the first dataset, the second dataset, the supplemental dataset, and/or any other dataset generated in Blocks S110, S120, and S130.

In receiving a supplemental dataset based on supplemental bioelectrical signals detected from a supplemental sensor module S130, the supplemental sensor module preferably includes an electromyography (EMG) sensor module configured to detect local muscle bioelectrical signals. Alternatively, the supplemental sensor module can include an accelerometer, gyroscope, and/or any sensor module facilitating implementation of the method 100. The supplemental sensor module preferably includes a supplemental electrode module that includes at least one electrode associated with at least one sensor channel (e.g., N sensor channels). In one example, the supplemental sensor module is an EMG sensor module that includes eight sensor channels, wherein each sensor channel corresponds to at least one electrode, and each sensor channel is configured to receive local muscle bioelectrical signals detected by the electrodes. Alternatively, the supplemental sensor module can include one or more units, wherein each unit is associated with a plurality of electrodes. However, the supplemental sensor module can be configured by any suitable means for detecting supplemental bioelectrical signals. The supplemental sensor module is preferably coupled to the user garment, and the supplemental sensor module preferably interfaces with the user to detect the supplemental bioelectrical signals. Alternatively supplemental sensor module can be detachably coupled to the user garment, or the supplemental sensor module can be embedded in or coupled to a supplemental user garment. However, the supplemental sensor module can interface with the user through any suitable means. Block S130 can additionally include providing a conductive medium (e.g., electrolyte gel) configured between electrical contacts and the body region(s) of the user. The conductive medium preferably enhances coupling between the user and the supplemental electrode module in facilitating signal transmission through the supplemental sensor channels. However, facilitating signal transmission can also be achieved by any other suitable means.

Figure 3B:
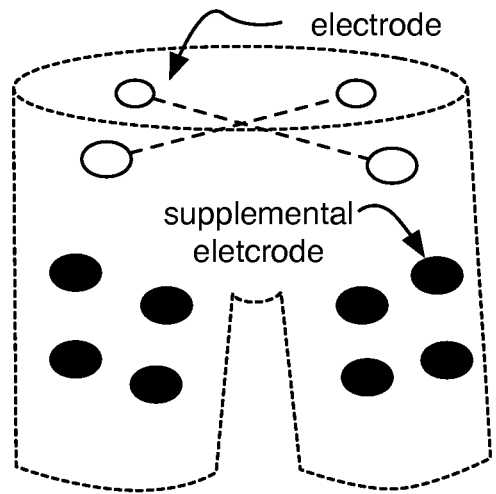

In a first variation, the supplemental sensor module is provided by way of the supplemental user garment, and the electrode module provided in Block S105 is provided by way of the user garment. The electrode module of the user garment can interface with the user at a first body region (e.g., the gluteus maximus muscles, the gluteus medius muscles, the vastus lateralis muscles, etc.), and the supplemental sensor module of the supplemental user garment can interface with the user at a second body region (e.g., the pectoralis muscles, the abdominal muscles, the oblique muscles, etc.). Alternatively, the electrode module of the user garment and the supplemental electrode module of the supplemental user garment can interface with the user at the same body region (e.g., the gluteus medius muscles). As shown in FIG. 3B, in a second variation, the electrode module provided in Block S105 and the supplemental sensor module can be provided by way of the same user garment. For instance, the user garment can take the form of a pair of shorts, and the electrode module and the supplemental sensor module can be embedded within the pair of shorts for interfacing with the user at groups of muscles substantially proximal to the gluteus maximus muscles. In some variations, the vectors between electrodes of the electrode module and the vectors between electrodes of the supplemental sensor module are positioned in a particular orientation (e.g., parallel, crossed, forming a square, etc.). Alternatively or additionally, the electrodes of the electrode module and the electrodes of the supplemental sensor module can lie substantially within the same plane (e.g., a transverse plane through the user). However, the electrodes of the supplemental sensor module can be oriented and/or positioned with respect to the user and/or the electrodes of the electrode module in any suitable manner.

1.3 Method—Generating a Noise-Mitigated Power Spectrum

Block S140 recites: generating a noise-mitigated power spectrum, which can be performed upon generating a combined dataset based upon a combination of the first dataset and the second dataset S142, calculating 1) a heart signal power spectrum based on the combined data set S144 and 2) a supplemental power spectrum based on the supplemental dataset S146, and generating a noise-mitigated power spectrum based on processing the heart signal power spectrum with the supplemental power spectrum S148. Block S142 can further include processing the combined dataset S143 with a signal processing algorithm configured to facilitate generation of an analysis of a beat parameter in Block S160. Block S140 functions to generate a noise-mitigated dataset in the frequency domain to facilitate the generation of an analysis of a beat parameter in Block S160. Block S140 is preferably performed at different components, but can also be performed at the same component. Blocks S142 and S143 are preferably performed at the processing subsystem, and Blocks S144, S146, and S148 are preferably performed at a mobile device (e.g., smart phone, head-mounted wearable computing device, wrist-coupled wearable computing device, etc.) of the user. The combined dataset of Block S142 and/or the processed combined dataset of Block S143 is preferably transmitted to the mobile device of the user through the communication subsystem. Alternatively, the combined dataset and/or the processed combined dataset can be locally stored at the system 200 and subsequently synced to the mobile device of the user. However, any suitable component and any number of suitable components can store datasets, process datasets, transmit datasets, and/or perform any block of method 100. In one variation, the first dataset of Block S110 and the second dataset of Block S120 can be processed at the processing subsystem, stored locally at the system 200, and transmitted to an alternative processing subsystem for performing Block S140, S142, S143, S144, and/or S146. In another variation, the combined dataset of S142 and/or the processed combined dataset of Block S143 can be transmitted to a cloud-based computing system for performing Block S140, S142, S143, S144, and/or S146.

1.3.1 Method—Generating a Combined Dataset

Block S142 recites: generating a combined dataset based upon a combination of the first dataset and the second dataset S142, which functions to combine and facilitate identification of correlations between data of the first dataset and the second dataset. Block S142 further functions to dampen a local noise component and to accentuate a signal component from the heart of the user from received data, thereby producing a noise-mitigated combined dataset. As such, the combined dataset can be used to isolate and separate signal components corresponding to a signal from the user's heart, from local noise (e.g., resulting from motion or activity of the user). The first and second dataset are preferably transmitted by the communication subsystem from the sensor channels to the processing subsystem for performing Block S142. However, the first and second dataset can be sent from, transmitted by, and received by any suitable component. Block S142 can further function to provide datasets from multiple sensor channels, which can be weighted based upon an assessment of quality of each of the datasets.

Figure 5B:
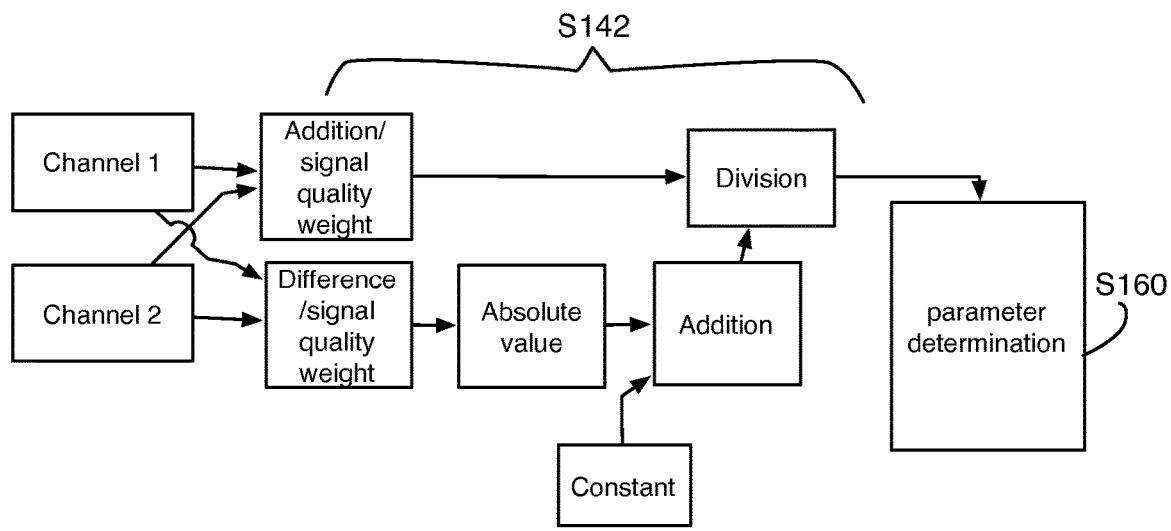
Figure 7A:
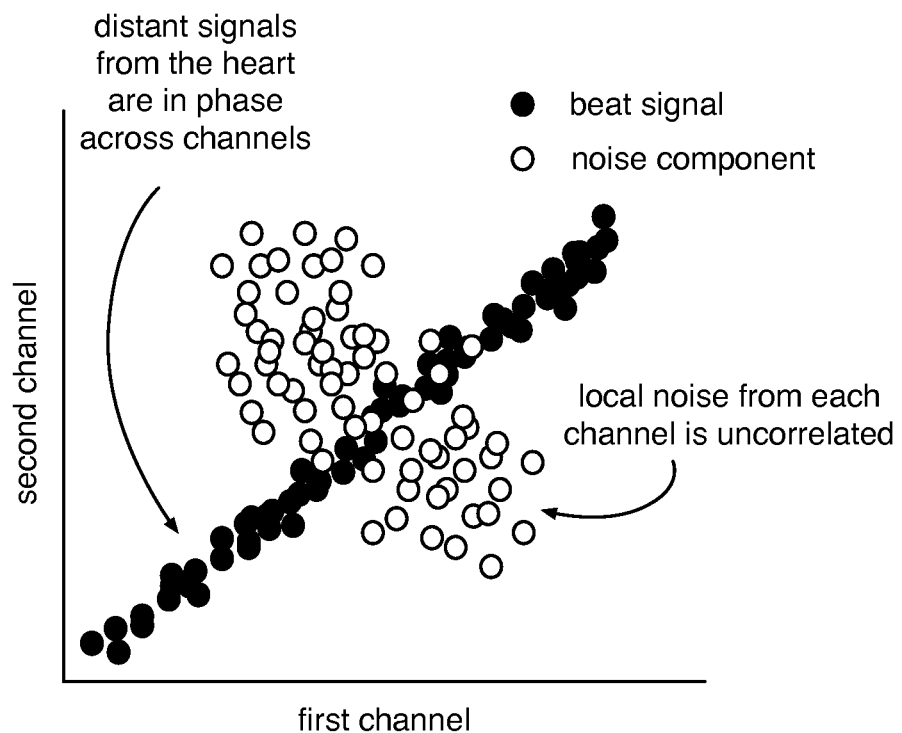
FIGS. 7A and 7B depict variations of noise distributions in relation to sensor channel number in an embodiment of a method for communicating beat parameters to a user.
Figure 7B:
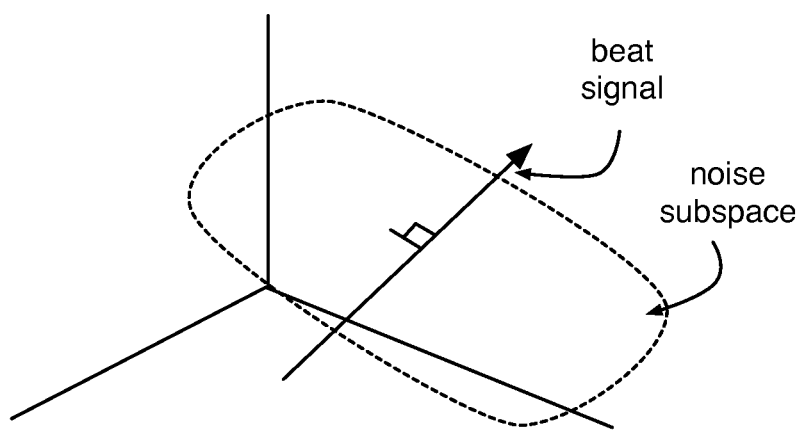
Figure 7C:
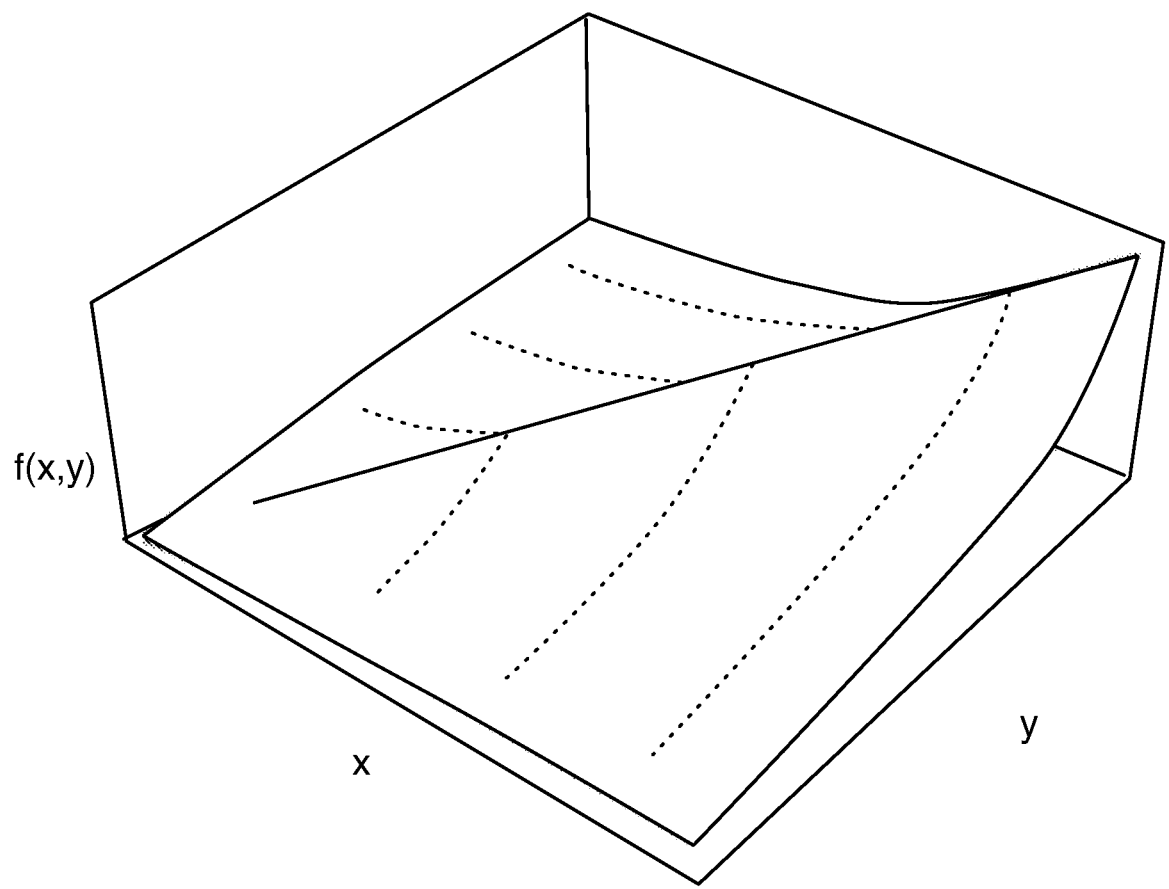
FIGS. 7C and 7D depict results of non-linear transformation processes that accentuate correlation between first and second datasets.
Figure 7D:
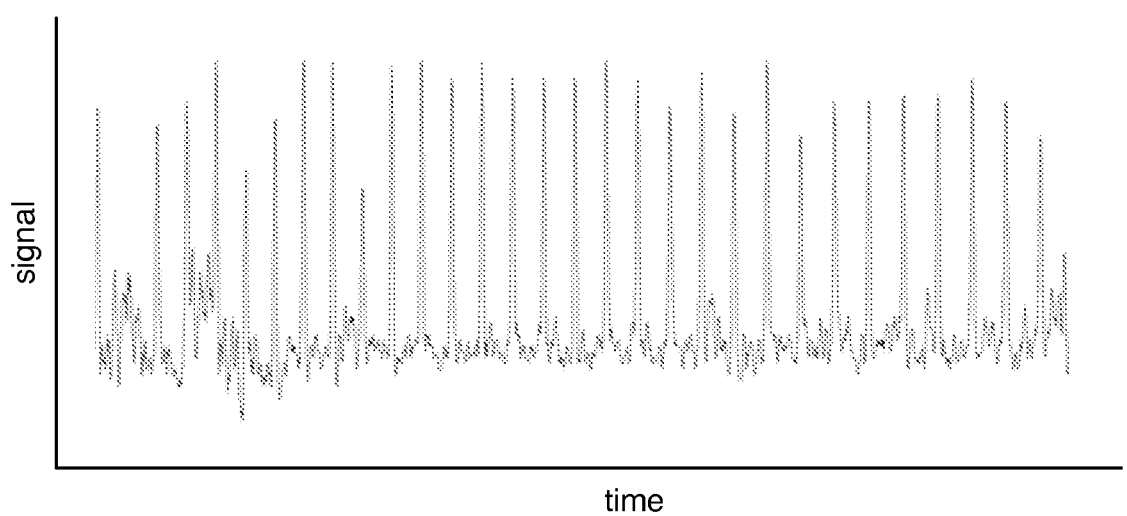

In variations, Block S142 can include any non-linear transformation of the first and second dataset. The non-linear transformations can be applied to the datasets as a whole or to subsets of the datasets. In a first variation of a non-linear transformation, Block S142 includes multiplying the first dataset and second dataset to produce a combined dataset. The combined dataset is then divided by a constant added to the absolute value of the difference of the first and second dataset. In more detail, a non-linear transformation $f(x,y)$ can be performed according to the following expression, where x is a signal from a first dataset and y is a signal from a second dataset: $f(x,y)=x*y/(1+|x-y|)$. An example of the resulting combined signal after the non-linear transform is shown in FIG. 7D. The resulting combined dataset accentuates a signal component from the heart of the user and facilitates extraction of a local noise component from received data, in generating a noise-mitigated dataset. In a second variation of a non-linear transformation, as shown in FIG. 5B, Block S142 comprises adding the first dataset and second dataset to produce a combined dataset. The combined dataset is then divided by a constant added to the absolute value of the difference of the first and second dataset. The combined resulting dataset accentuates a signal component from the heart of the user and facilitates extraction of a local noise component from received data, in generating a noise-mitigated dataset. As such, Block S142 utilizes stronger correlations between signals from the heart of the user and weaker correlations in noise from the sensor channels, due to the channel configurations and position of the electrodes noted in relation to Blocks S110 and S120. FIG. 7C shows how the non-linear transform described above accentuates the correlation between the first (x) and second (y) datasets. An example of the resulting combined signal after the non-linear transform is shown as $f(x,y)$ in FIG. 7C.

In the first, second, and other variations, Block S142 can include performing an assessment of quality of the conditioned dataset(s) of Block S135 and/or the dataset(s) received in Blocks S110 and S120, in order to tag the dataset(s) with a weight associated with dataset quality. The assessment can be based upon any one or more of: a determination of a signal-to-noise ratio present in a dataset, a determination of a degree of correlation between datasets derived from Blocks S110 and S120, a determination of an amount of motion artifacts present in a dataset, a determination of an amount of interference (e.g., from a sensor configured proximal to electrodes of one unit) affecting a dataset, an assessment of any malfunction (e.g., due to a faulty electrode contact) in generation of a dataset, and an assessment of any other suitable factor contributing to signal quality. The weight(s) can then be applied to their corresponding datasets prior to combination (e.g., by addition), which produces a combined dataset. Other variations of the first example, however, can include any other suitable combination of weighting and combination of datasets to produce the combined dataset of Block S142. The first and second dataset can otherwise be combined in any other suitable manner.

Furthermore, in variations of the method 100 including reception of more than two datasets in Blocks S110 and S120, Block S142 can include weighting the datasets and combining (e.g., multiplying) the datasets in any suitable sequence and/or number of times. For instance, one variation can include weighting two datasets, combining the two datasets, and combining the two datasets with a third weighted dataset. Another variation can include combining two unweighted datasets, weighting the combined dataset and weighting a third dataset, and combining the combined dataset with the third weighted dataset. Block S142 can, however, additionally or alternatively include any other suitable manipulation and combination of two or more datasets received in Blocks S110 and S120.

Figure 6A:
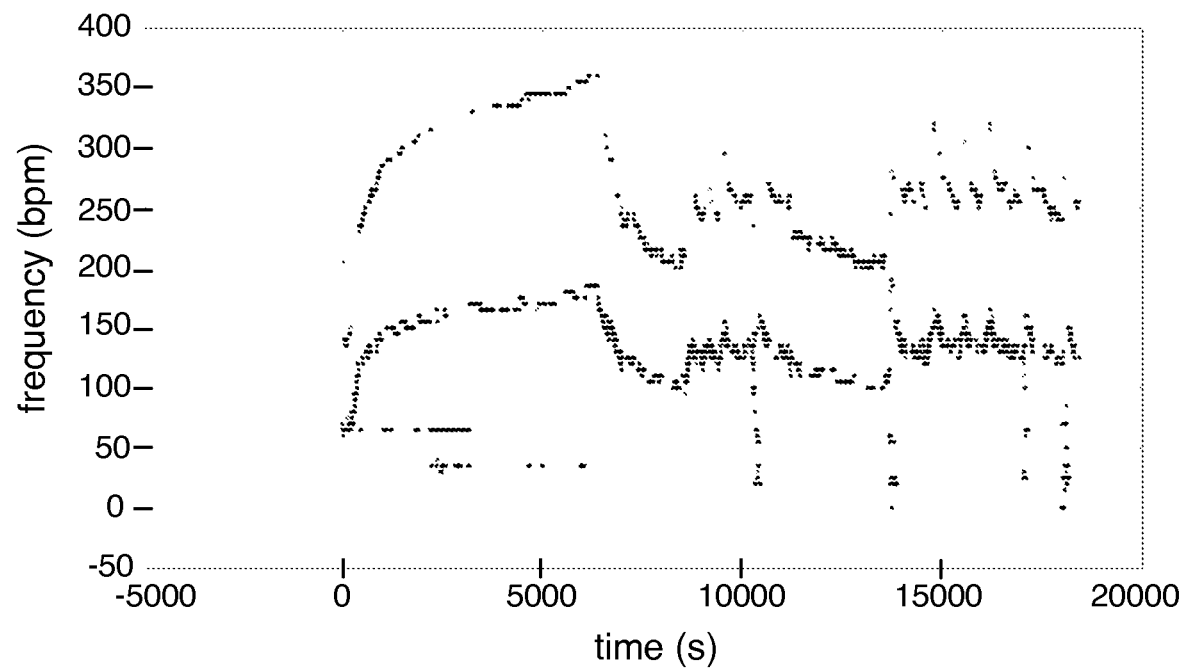
FIGS. 6A and 6B depict variations of processing signal components with harmonic signals in an embodiment of a method for communicating beat parameters to a user.

As shown in FIG. 6A, in variations of Block S144, calculating a heart signal power spectrum includes combining a first or fundamental frequency component of the combined heart signal dataset with a second frequency component that is a harmonic of the first frequency component. The harmonic frequency is preferably a component frequency of the first or fundamental frequency component, wherein the component frequency is an integer multiple of the fundamental frequency (e.g., 2f, 3f, 4f, etc. where f denotes the fundamental frequency). Combining the first frequency component with a corresponding harmonic frequency can be performed through a non-linear (e.g., by dividing the frequency component and the corresponding harmonic frequency) or linear combination (e.g., by summing the frequency component and corresponding harmonic frequency), but the frequency component and the harmonic frequency can be combined or processed in any other suitable manner. The harmonic frequency is preferably a $2^{nd}$ harmonic (i.e., 2f), but can be any other integer multiple of the fundamental frequency.

Block S142 can further include processing the combined dataset S143 with a signal processing algorithm configured to facilitate generation of an analysis of a beat parameter in Block S160. Block S143 functions to process the combined dataset with at least one signal processing algorithm and/or additional data from sensors associated with the electrode module, in order to further enhance noise reduction and/or facilitate extraction of one or more beat parameters from an output of Block S142. As such, in Blocks S142 and S143, identification of the local noise component(s) can be based upon correlation (e.g., cross-correlation) or convolution between the first and the second datasets of Blocks S110 and S120, wherein noise components of the dataset can be separated upon observation of a high degree of correlation between a first dataset and a second dataset. In an example, a heart beat signal component has a high degree of correlation across a first dataset and a second dataset of the combined dataset, while noise components are approximately orthogonal to the heart beat signal component. In this example, orthogonality to the heart beat signal component can thus be used to separate and extract at least a portion of noise from the combined dataset, as shown in FIGS. 7A and 7B. In particular, for N channels in a multidimensional space, each channel substantially synchronized to the same heart beat signal, an (N−1) dimensional subspace that is orthogonal to the heart beat signal component can be determined as a "noise removed subspace". Thus, as shown in FIG. 7A, two channels produce a 1-dimensional noise removed subspace that is orthogonal to a vector corresponding to the heart beat signal component, and as shown in FIG. 7B, three channels produce a 2-dimensional noise removed subspace that is approximately orthogonal to a vector corresponding to the heart beat signal component. Thus, noise-extraction performance according to the method 100 increases with a greater number of channels, as the probability increases that a greater amount of noise falls within a noise removed subspace (e.g., an orthogonal subspace). In the variations described, there is greater probability that noise will fall in a 2-D planar subspace with three channels than along a 1-D linear subspace with two channels.

In variations of Block S143, identification of a noise removed subspace can further include identification of contributors to the noise removed subspace, wherein the contributors can include any one or more of: friction induced by motion of the user, gross muscle movements of the user, electrode placement, friction of a garment within which electrodes are integrated and which is coupled to the user, and any other suitable noise contributor. Identification of contributors can be facilitated or supplemented by the supplemental dataset received in Block S130, wherein the supplemental sensor module (e.g., accelerometers, EMG sensors, gyroscopes, etc.) can be utilized to provide adaptive filtering. For instance, EMG sensors located near electrodes of the electrode module or at other points of interest on the user's body (e.g., located proximal the gluteus maximus muscles, located proximal the vastus lateralis muscles) can be used to identify and filter out contribution of and effects of local muscles in generating signal noise. In another example, an accelerometer and/or a gyroscope associated with the electrode module of Blocks S105 can be used to generate a gross motion signal of the user (e.g., including signals resulting from impacts during cardio exercise), which can be used to identify contribution of and effects of motion and/or friction in generating signal noise. Additionally or alternatively, in variations, adaptive filtering techniques leveraging motion signals from additional sensors (e.g., accelerometers or gyroscopes), as well as close proximity EMG signals could be processed with the first dataset, the second dataset, and/or any other dataset in facilitating the generation of the beat parameter analysis S160. Alternatively, any suitable means of adaptive filtering can be applied on any suitable dataset.

Figure 8:
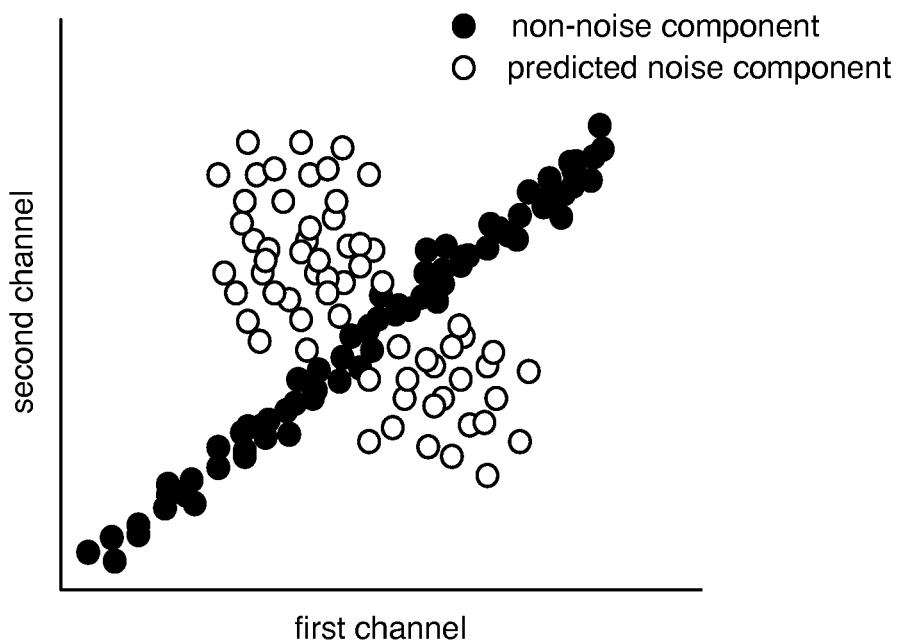
FIG. 8 depicts an example of predictions of noise components in an embodiment of a method for communicating beat parameters to a user.

As shown in FIG. 8, in any of these examples and variations, contribution and/or effects of contributors to the noise subspace can be used to enhance removal of noise within the combined dataset based upon a machine learning algorithm that is trained with a training dataset. The training dataset can include example noise components with associated contributors, which can be used to facilitate identification of and removal of noise, resulting from the contributors, in additional datasets received from sensor channels of the electrode module coupled to the user. In variations, the machine learning algorithm can be characterized by a learning style including any one or more of: supervised learning (e.g., using logistic regression, using back propagation neural networks), unsupervised learning (e.g., using an Apriori algorithm, using K-means clustering), semi-supervised learning, reinforcement learning (e.g., using a Q-learning algorithm, using temporal difference learning), and any other suitable learning style. Furthermore, the machine learning algorithm can implement any one or more of: a regression algorithm (e.g., ordinary least squares, logistic regression, stepwise regression, multivariate adaptive regression splines, locally estimated scatterplot smoothing, etc.), an instance-based method (e.g., k-nearest neighbor, learning vector quantization, self-organizing map, etc.), a regularization method (e.g., ridge regression, least absolute shrinkage and selection operator, elastic net, etc.), a decision tree learning method (e.g., classification and regression tree, iterative dichotomiser 3, C4.5, chi-squared automatic interaction detection, decision stump, random forest, multivariate adaptive regression splines, gradient boosting machines, etc.), a Bayesian method (e.g., naïve Bayes, averaged one-dependence estimators, Bayesian belief network, etc.), a kernel method (e.g., a support vector machine, a radial basis function, a linear discriminate analysis, etc.), a clustering method (e.g., k-means clustering, expectation maximization, etc.), an associated rule learning algorithm (e.g., an Apriori algorithm, an Eclat algorithm, etc.), an artificial neural network model (e.g., a Perceptron method, a back-propagation method, a Hopfield network method, a self-organizing map method, a learning vector quantization method, etc.), a deep learning algorithm (e.g., a restricted Boltzmann machine, a deep belief network method, a convolution network method, a stacked auto-encoder method, etc.), a dimensionality reduction method (e.g., principal component analysis, partial lest squares regression, Sammon mapping, multidimensional scaling, projection pursuit, etc.), an ensemble method (e.g., boosting, boostrapped aggregation, AdaBoost, stacked generalization, gradient boosting machine method, random forest method, etc.), and any suitable form of machine learning algorithm.

1.3.2 Method—Calculating a Heart Signal Power Spectrum and a Supplemental Power Spectrum Block S144 recites: calculating a heart signal power spectrum based on the combined data set; and Block S146 recites: calculating a supplemental power spectrum based on the supplemental dataset. Block S144 functions to transform the combined data set into the frequency domain to facilitate the generation of the beat parameter analysis S160. Block S146 functions to transform the supplemental data set—received in Block S130—into the frequency domain for use in isolating and separating noise (e.g., locally-induced noise) from the signals of interest. The heart signal power spectrum and the supplemental power spectrum preferably represent heart signal power and supplemental signal power falling within different frequency bins. The combined data set and the supplemental dataset are preferably transformed into the heart signal power spectrum and the supplemental power spectrum, respectively, through a Fourier transform (e.g., discrete Fourier transform (DFT), fast Fourier transform (FFT), etc.). In one embodiment, a frequency domain approach based on the DFT can be used to approximate the heart rate of the user by calculating the fundamental frequency corresponding to the R-R period of the QRS complex of the heart beat signal. An approximation of the DFT can be an efficient means of calculating the dominant frequency of an input signal on a resource constrained embedded system. Additionally or alternatively, any other suitable signal processing algorithm configured to evaluate a transform of the heart signal and/or the supplemental signals, including one or more of: a wavelet transform algorithm, a McAulay-Quatari analysis, a sparse Fourier transform algorithm, a maximum entropy method, and any other algorithm can be used in Block S145 to determine a transform of signals. Alternatively, a time based QRS detection approach could be used on the non-linear input inclusive or exclusive of a combination of derivatives, amplitude thresholds and/or QRS template matching.

Figure 9A:
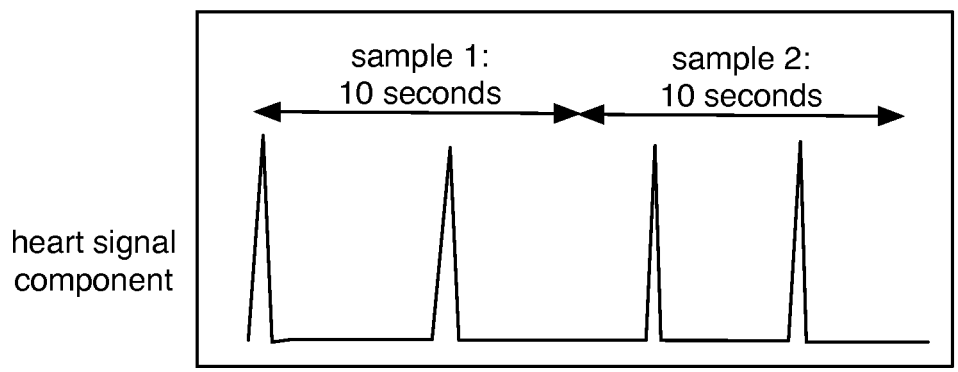
FIGS. 9A and 9B depict variations of segmenting a signal component into samples across time intervals in an embodiment of a method for communicating beat parameters to a user.
Figure 9B:
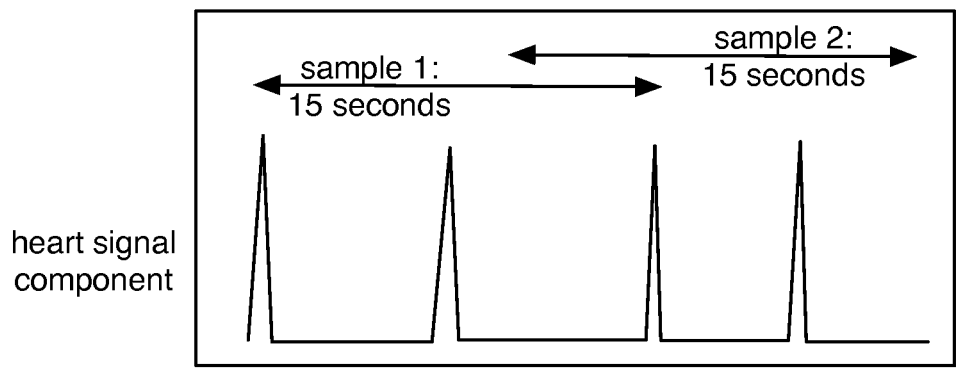

As shown in FIGS. 9A and 9B, in some variations of Block S144, calculating the heart signal power spectrum S144 includes calculating the heart signal power spectrum based on a sample of the combined dataset. The sample preferably includes a heart signal component segment corresponding to a time interval associated with a predetermined time interval length (e.g., 5 second intervals, 10 second intervals, 12 second intervals, etc.). Alternatively, the time interval length can be user-determined, dynamically changed (e.g., changing from 5 second intervals to 10 second intervals during signal detection), adaptively adjusted (e.g., updated in response to current user body temperature, heart rate, EMG signals, signal-to-noise ratio, etc.), learned (e.g., based on training data with features predictive of time interval lengths that—when used to sample the signal—can increase heart rate accuracy). However, the time interval length can be determined by any other suitable means. In variations where multiple heart signal power spectrums are calculated for multiple samples, the multiple heart signal power spectrums can be combined non-linearly (e.g., by multiplying together the heart signal power spectrums) or linearly (by summing the heart power spectrums) to form a power spectral density. Alternatively, the multiple heart signal power spectrums can be combined or used in any other manner. As shown in FIG. 9A, in a first variation, the time intervals are non-overlapping such that there is no signal redundancy between samples of the combined dataset. The time intervals are preferably contiguous. In an example of the first variation, sampling is performed in 10 second time intervals, such that samples correspond to the signal component at time intervals of 0-10 seconds, 11-20 seconds, 21-30 seconds, etc. Alternatively, the time intervals can be non-contiguous (e.g. 0-10 seconds, 15-25 seconds, 30-40 seconds, etc.), but the set of samples can also include a combination of contiguous and non-contiguous time intervals (e.g., 0-5 seconds, 6-10 seconds, 15-20 seconds, etc.). As shown in FIG. 9B, in a second variation, the time intervals are overlapping such that there is signal redundancy between samples of the combined dataset. In an example of the second variation, sampling is performed in 15 second time intervals with a 5 second overlap between two subsequent samples. In the example of the second variation, samples correspond to the signal component at time intervals of 0-15 seconds, 11-25 seconds, 21-35 seconds, etc. However, the combined dataset can be sampled in any other suitable manner, and sampling can also be performed on one or more outputs of one or more of Blocks S110, S120, S130, S140, S142, S144, S146, S148, and/or any other suitable outputs.

Figure 10:
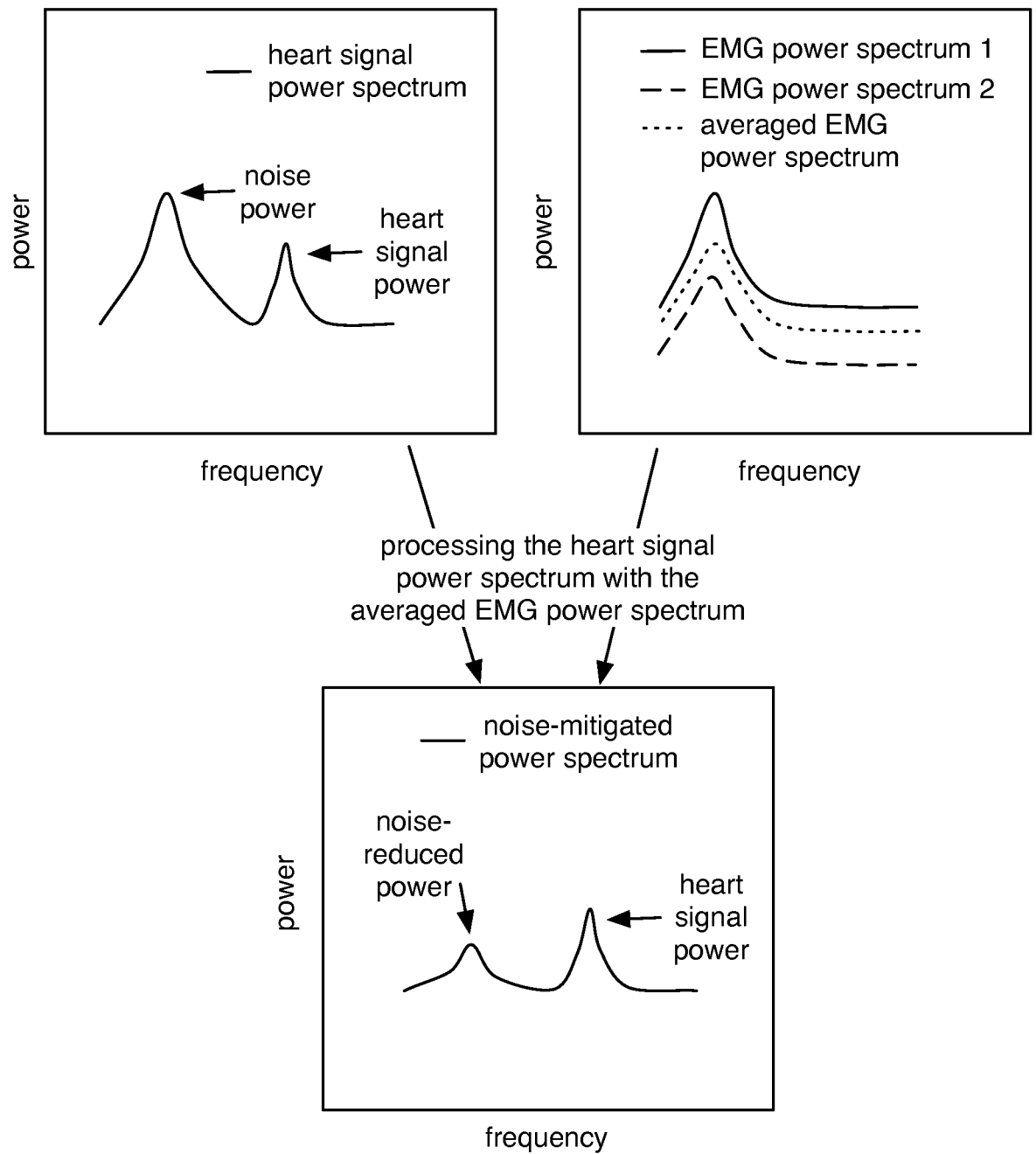
FIG. 10 depicts an example of combining and processing power spectrums in an embodiment of a method for communicating beat parameters to a user.

As shown in FIG. 10, in some variations of Block S146, calculating the supplemental power spectrum can include combining a plurality of supplemental power spectrums calculated from individual supplemental signals included in the supplemental dataset. For example, the supplemental sensor module can be an EMG sensor module including eight EMG sensor channels, and individual power spectrums can be calculated based on signals from each of the eight EMG sensor channels. The individual power spectrums can then be averaged to generate the supplemental power spectrum, as shown in FIG. 10 (where, for purposes of illustration, averaging of two power spectra is shown). In other variations of Block S146, calculating the supplemental power spectrum can include combining individual supplemental signals into a combined supplemental signal, and performing a transformation on the combined supplemental signal to generate the supplemental power spectrum. Supplemental signals and/or power spectrums derived from supplemental signals can be combined non-linearly (e.g., by multiplying together the supplemental signals, by multiplying together the power spectrums derived from supplemental signals) or linearly (e.g., by summing the supplemental signals, by summing together the power spectrums derived from supplemental signals). However, the supplemental power spectrum can be generated by any suitable means of combining supplemental signals or power spectrums derived from supplemental signals.

Figure 6B:
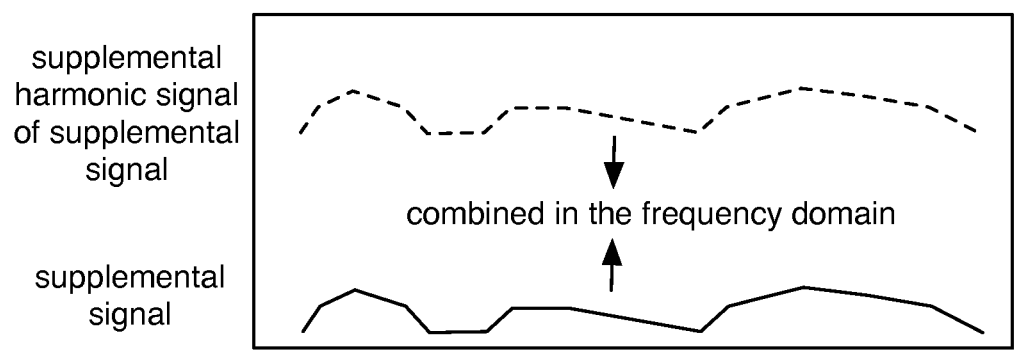

As shown in FIG. 6B, in some variations of Block S146, calculating a supplemental power spectrum can include combining frequency components from the supplemental dataset with harmonic components of the supplemental dataset. Combining the supplemental first or fundamental frequency component with the corresponding supplemental harmonic component can be performed through a non-linear (e.g., by dividing the frequency component and the corresponding harmonic frequency component) or linear combination (e.g., by summing the frequency component and the corresponding harmonic frequency component). In a first variation, the supplemental sensor module includes one or more supplemental sensor channels receiving one or more supplemental signals, and transformed into one or more supplemental signal power spectra. The frequency components of the individual power spectra are then combined with their corresponding harmonic frequency components. In a second variation the individual supplemental power spectra are combined into a combined supplemental power spectrum (e.g. summation of the power spectra from individual supplemental signals). A first fundamental frequency component is combined with a corresponding harmonic frequency of the combined supplemental power spectrum. However, combining the supplemental spectra frequency components with supplemental harmonic frequency components can be additionally or alternatively performed in any other suitable manner.

1.3.3 Method—Generating a Noise-Mitigated Power Spectrum

As shown in FIG. 10, Block S148 recites: generating a noise-mitigated power spectrum based on processing the heart signal power spectrum with the supplemental power spectrum S148, which functions to generate a noise-mitigated dataset from which to derive the beat parameter analysis S160. Block S148 further functions to dampen a noise component of the heart signal power spectrum, and to accentuate a heart signal component of the heart signal power spectrum. The heart signal power spectrum and the supplemental power spectrum are preferably processed through combining the power spectrums, wherein the combination can be non-linear (e.g., by dividing the heart signal power spectrum by the supplemental power spectrum) or linear (e.g., by subtracting the supplemental power spectrum from the heart power spectrum).

In one variation, generating the noise-mitigated power spectrum includes smoothing power spikes in the noise-mitigated power spectrum. Smoothing power spikes is preferably performed by applying an exponential moving average, which can be calculated as:

$$EMA_k = \gamma^*(EMA_{k-1}) + (1-\gamma)^*x[k]$$

wherein $EMA_k$ is the exponential moving average at a time period k, coefficient $\gamma$ is the degree of weighting decrease, and x[k] is the value at time period k. However, other smoothing algorithms can additionally or alternatively be applied. Applying smoothing algorithms to smooth power spikes can also be performed on power spectrums from Blocks S144, S146, and/or any other suitable block of the method 100.

1.4 Method—Generating a Beat Parameter Analysis

Block S160 recites: generating an analysis of a beat parameter S160, which functions to extract at least one parameter, characterizing the user's heart rate during a period of activity or rest, from initially noisy datasets. The beat parameter analysis is preferably generated at the processing subsystem, but any other suitable component can generate the beat parameter analysis. Generating the beat parameter analysis S160 is preferably based upon the noise-mitigated power spectrum generated in Block S140. Alternatively, generating the beat parameter analysis can be based on any signal output of Block S140, S142, S143, S144, S146, S148, and/or any other block. In a first example, generating the beat parameter analysis includes identifying a frequency parameter with highest power in the noise-mitigated power spectrum, and generating a beat parameter analysis (e.g., an analysis of heart rate) based upon the frequency parameter with highest power. In a second example, generating the beat parameter analysis includes calculating a heart rate variability across the time intervals determined in variations of Block S144 above, examples of which are shown in FIGS. 9A and 9B. In the second example, multiple heart rates are calculated from a set of power spectrums derived from a set of samples corresponding to determined time intervals. The heart rate variability is then calculated based on the multiple heart rates, each associate with a distinct time interval of a set of time intervals. However, the beat parameter analysis can be generated based on a noise-mitigated dataset in any suitable manner.

Figure 11A:
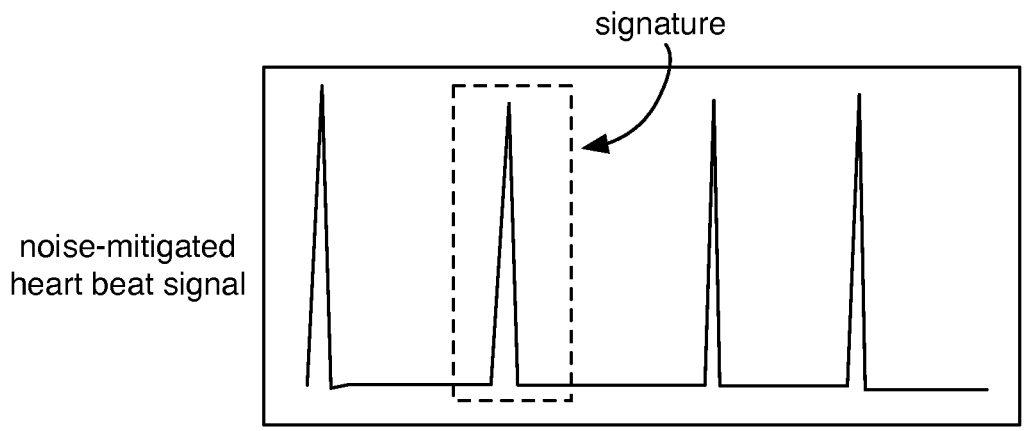
FIGS. 11A and 11B depict variations of signatures of a beat signal in an embodiment of a method for communicating beat parameters to a user.
Figure 11B:
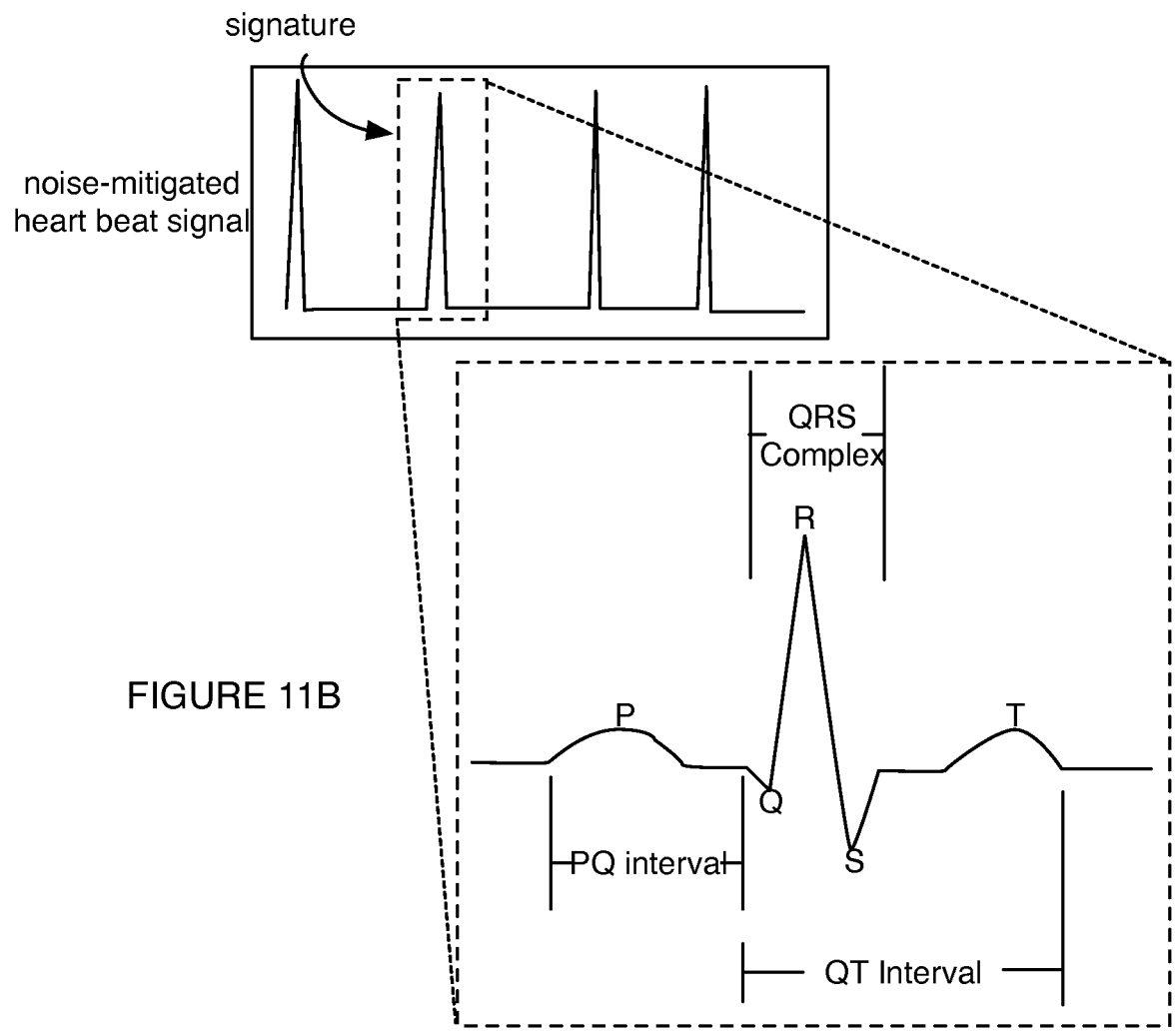

Block S160 can additionally include identifying a set of signatures within a noise-mitigated heart signal output of Block S140, S142, S143, S144, S146, and/or S148, wherein at least one signature of the set of signatures corresponds to a single pulse or phase of beats of the user's heart. As such, the set of signatures can include peaks within the noise-mitigated heart beat signal, as shown in FIG. 11A, valleys within the noise-mitigated heart beat signal, and/or a set of features (e.g., peaks and valleys corresponding to a QRS complex) within the noise-mitigated heart beat signal as shown in FIG. 11B. In Block S160, frequencies at which one or more signatures occur within the noise-mitigated heart beat signal can then be used to determine the heart rate parameter and/or any other suitable parameter derived from beats of the user's heart. For instance, identified signatures can be used to determine any one or more of beat duration, beat irregularity, beat frequency (i.e., heart rate), instantaneous beat interval (R-R) from shape and/or frequency components of the noise-mitigated heart beat signal. Such parameters can then be used to notify a user or other entity associated with the user regarding parameters of his/her heart beat in a dynamic manner, and to notify the user (or entity) regarding irregularities in heart beat. However, the beat parameter analysis can be determined in any other suitable manner, such as generating the beat parameter analysis without identifying the set of signatures.

In variations of Block S160, determination of signal shape and duration characteristics from a signature corresponding to a phase of beats can be used to determine parameters derived from one or more QRS complexes of the user's beating heart. In one variation, Block S160 can further include generating values of QT characteristics, as shown in FIGS. 11A and 11B, from a signature corresponding to a QRS complex. For instance, upon determination of a beat duration, an initiation of a beat can correspond to the QRS complex (e.g., the initiation of the QRS complex), and a termination of a beat can correspond to a T-wave feature (e.g., a termination of a T wave). Thus, a QT interval, which is defined as a measure of time between the start of a QRS complex and the end of a T wave in a cardiac cycle, can be estimated based upon the beat duration from a signature. Any other suitable parameter derived from Q, R, and/or S features of a QRS complex (e.g., an R-R interval) or any other suitable portion of a cardiac cycle can be determined in Block S160.

Figure 13:
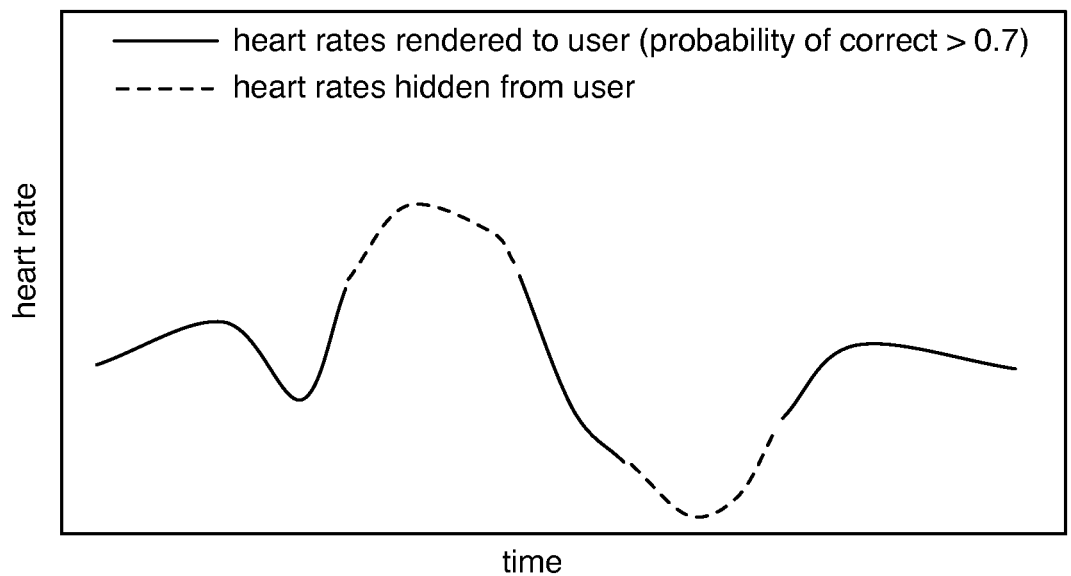
FIG. 13 depicts an example of rendering information based on a confidence parameter in an embodiment of a method for communicating beat parameters to a user.

As shown in FIG. 13, in some variations of Block S160, generating the beat parameter analysis includes predicting a confidence parameter indicating an accuracy level of the beat parameter. Prediction of the confidence parameter is preferably performed at the processing subsystem (e.g., as described in Section 2 below), but any other suitable system component can predict the confidence parameter. The confidence parameter can include one or more of: a probability that the beat parameter is correct when compared to a ground truth, a false negative rate, a false positive rate, and/or any other suitable confidence parameter. Predicting the confidence parameter is preferably based on running a predictive model trained on features predictive of the beat parameter accuracy level. The feature types predictive of the beat parameter accuracy level can include or be derived from any one or more of: average heart rate, current heart rate, max or min heart rate within a time interval, ratio of top power values to lower power values in a power spectrum, max power value, Wiener entropy, impedance, impedance variability, and any other predictive feature.

The predictive model used to predict the confidence parameter is, in a specific example, generated using linear regression-based analyses, logistic regression-based analyses, and random forest models. However, the predictive model used to predict the confidence parameter can additionally or alternatively be based on a machine learning algorithm, which can be characterized by a learning style including any one or more of: supervised learning (e.g., using logistic regression, using back propagation neural networks), unsupervised learning (e.g., using an Apriori algorithm, using K-means clustering), semi-supervised learning, reinforcement learning (e.g., using a Q-learning algorithm, using temporal difference learning), and any other suitable learning style. Furthermore, the machine learning algorithm can implement any one or more of: a regression algorithm (e.g., ordinary least squares, logistic regression, stepwise regression, multivariate adaptive regression splines, locally estimated scatterplot smoothing, etc.), an instance-based method (e.g., k-nearest neighbor, learning vector quantization, self-organizing map, etc.), a regularization method (e.g., ridge regression, least absolute shrinkage and selection operator, elastic net, etc.), a decision tree learning method (e.g., classification and regression tree, iterative dichotomiser 3, C4.5, chi-squared automatic interaction detection, decision stump, random forest, multivariate adaptive regression splines, gradient boosting machines, etc.), a Bayesian method (e.g., naïve Bayes, averaged one-dependence estimators, Bayesian belief network, etc.), a kernel method (e.g., a support vector machine, a radial basis function, a linear discriminate analysis, etc.), a clustering method (e.g., k-means clustering, expectation maximization, etc.), an associated rule learning algorithm (e.g., an Apriori algorithm, an Eclat algorithm, etc.), an artificial neural network model (e.g., a Perceptron method, a back-propagation method, a Hopfield network method, a self-organizing map method, a learning vector quantization method, etc.), a deep learning algorithm (e.g., a restricted Boltzmann machine, a deep belief network method, a convolution network method, a stacked auto-encoder method, etc.), a dimensionality reduction method (e.g., principal component analysis, partial lest squares regression, Sammon mapping, multidimensional scaling, projection pursuit, etc.), an ensemble method (e.g., boosting, boostrapped aggregation, AdaBoost, stacked generalization, gradient boosting machine method, random forest method, etc.), and any suitable form of machine learning algorithm. However, predicting the confidence parameter can be performed through any other suitable means.

In one variation, a logistic regression model can be used to predict a confidence parameter for a calculated user heart rate derived from the noise-mitigated power spectrum. The model can be trained on data containing a set of labels (e.g., binary dependent variables for a logistic regression model), where each label can be the absolute difference between a previously estimated heart rate (e.g., a heart rate previously generated from blocks of method 100, a heart rate generated using a device that provides training data, etc.) and a ground truth heart rate. Each label in the set of labels can be associated with a set of features (e.g., a Weiner entropy of 0.5) corresponding to a set of predictive feature types (e.g., Weiner entropy). Upon training the model, the model can be used to predict the probabilities that heart rates at different time points are correct. The model output can be smoothed (e.g., by exponential average), filtered, and/or processed by any other means. For example, an exponential average can be applied to smooth the model output. Manual filters can then be applied based on signal characteristics that are known to indicate a poor signal (e.g., filtering signals associated with an estimated heart rate is below 54 bpm, filtering signals associated with a contact quality or impedance higher than a given threshold that corresponds to poor contact between the sensor and body of the user, filtering signals associated with a lower sampling rate threshold, filtering signals associated with a higher sampling rate threshold, etc.). A second exponential average can then be applied after the manual filtering to further smooth the output. However, any other model type, label type, feature type, and/or processing operation can be used to predict the confidence parameter for a calculated user heart rate.

1.5 Method—Rendering Information

Figure 12:
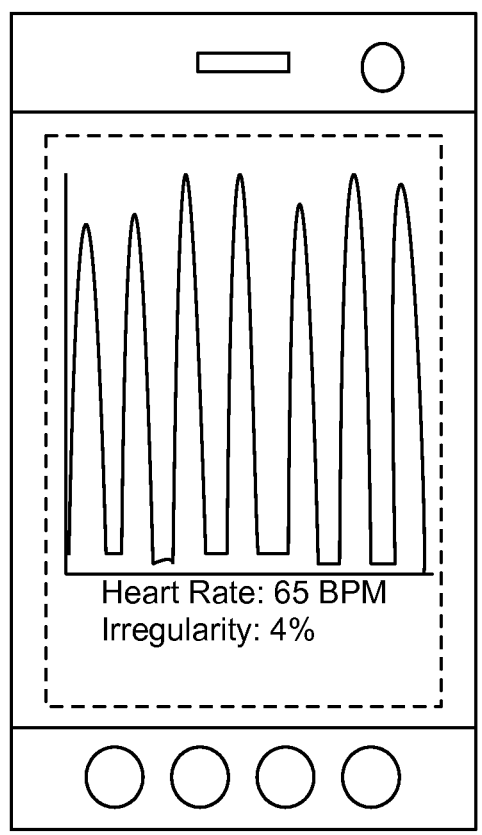
FIG. 12 depicts an example user interface for receiving information in an embodiment of a method for communicating beat parameters to a user.

Block S170 recites: rendering information derived from the beat parameter analysis to the user at the user interface, which functions to inform the user of any beat parameters or irregularities in the beat parameter(s) determined in Block S160. In Block S170, information from the analysis is preferably determined and provided to the user substantially continuously and in near real-time, such that the user or other entity can directly associate performed activities with heart beat behavior. The information can be provided in any one or more of: a visual manner, as shown in FIG. 12, an audio manner, a haptic manner, and in any other suitable manner. The information is preferably provided at an electronic device (e.g., mobile device, personal computer, wearable computing device, tablet, etc.) of the user, but can additionally or alternatively be provided to the user in a non-electronic manner. Preferably, the information is provided by way of an application executing at a mobile device (e.g., smart phone, head-mounted wearable computing device, wrist-coupled wearable computing device, etc.) of the user, including a display configured to graphically display visual and/or textual information related to the analysis. However, in variations, the information can be provided at any other suitable device and/or in any other suitable manner.

In relation to irregularities or other features of interest of the analysis, Block S170 can include sending a notification to the user. In one variation, the notification can be provided at a messaging client (e.g., text messaging client, email client, etc.), accessible by the user at a mobile device and/or a personal computer of the user. In another variation, the notification can be provided using a vibration motor of an electronic device of the user. However, the notification can be provided in any other suitable manner. Furthermore, in some variations, the notification can additionally or alternatively be provided to an entity associated with the user, in order to inform another entity of a state of the user. In variations, the entity can be any one or more of: a trainer, a coach, a parent, a sibling, a significant other, a healthcare provider, a supervisor, a peer, and any other suitable entity associated with the user. As such, the entity can be notified regarding a health condition (e.g., heart rate outside a target heart range, heart rate variability above a determined threshold, estimated number of calories burned, etc.), related to the user's cardiovascular health. However, the notification can indicate any suitable information or health condition to the user.

As shown in FIG. 13, in some variations of Block 170, rendering information derived from the beat parameter analysis S170 includes rendering information based on the confidence parameter calculated in variations of S160 above. The information is preferably rendered when the confidence parameter is above a determined threshold (e.g., the information will be rendered if the probability of a correct estimated heart rate is above 0.7), and the information is withheld from rendering otherwise. The threshold can be predetermined (e.g., probability of a correct beat parameter is greater than 0.7), user-determined, dynamically calculated (e.g., the threshold is adjusted based on the current user temperature, time of day, strength of electrical contact between the electrodes and the user), learned (e.g., based on data indicating different levels of user satisfaction depending on the confidence parameter threshold chosen for rendering heart rate information to the user), and/or determined in any other suitable manner. Additionally or alternatively, rendering information can be based on any other suitable criteria with respect to the confidence parameter.

The method 100 can, however, include any other suitable blocks or steps configured to process a noise-mitigated dataset from a noisy dataset, and/or to determine and provide heart beat information from the noise-mitigated dataset. Furthermore, as a person skilled in the art will recognize from the previous detailed description and from the figures and claims, modifications and changes can be made to the method 100 without departing from the scope of the method 100.

2. System

Figure 14:
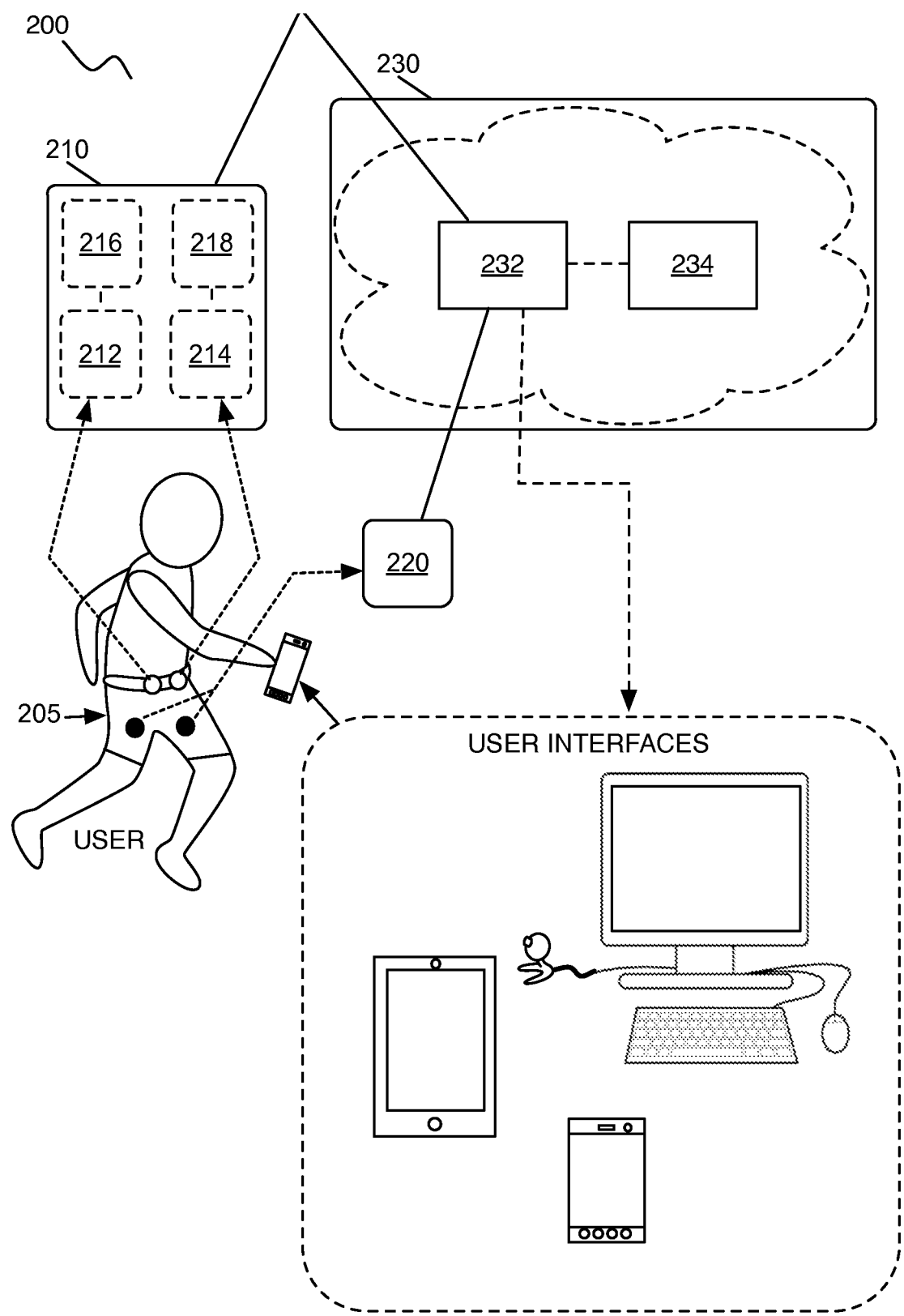
FIG. 14 depicts an embodiment of a system for communicating beat parameters to a user.

As shown in FIG. 14, a system 200 for communicating beat parameters to a user at a user interface of an electronic device associated with user includes: a garment 205 configured to be worn by the user at a first body region; a sensor module 210 coupled to the garment and comprising: a first electrode pair 212, a second electrode pair 214, a first sensor channel 216 associated with the first electrode pair, and configured to generate a first dataset based on a first set of detected bioelectrical signals, and a second sensor channel 218 associated with the second electrode pair, and configured to generate a second dataset based on a second set of detected bioelectrical signals, wherein the first dataset and the second dataset comprise a local noise component and a heart signal component; a supplemental sensor module 220 configured to generate a supplemental dataset based on supplemental signals; and a control module 230 comprising: a communication subsystem 232 in communication with the sensor module and the supplemental sensor module, and a processing subsystem 234 in communication with the communication subsystem, and configured to: generate a combined dataset based upon a combination of the first dataset and the second dataset, calculate 1) a heart signal power spectrum based on the combined data set, and 2) a supplemental power spectrum based on the supplemental dataset, generate a noise-mitigated power spectrum based on processing the heart signal power spectrum with the supplemental power spectrum, generate an analysis of a beat parameter based upon the frequency parameter with highest power, and generate information to be rendered to the user at the user interface, wherein the information is derived from the beat parameter analysis.

The system 200 functions to enable extraction of a beat parameter (e.g., heart beat parameter, pulse parameter, heart rate) based upon processing multiple sensor channels of the sensor module 210 in a manner that removes local noise effects resulting from placement of electrodes of the sensor module 210. In a specific example, the system 200 is configured to enable extraction of heart beat parameters from a user in near real-time, from multiple electrode channels of electrodes placed at or below the waistline of the user, while the user is performing a physical activity (e.g., exercising, weight lifting, etc.). The processing subsystem 234 of the control module 230 in this specific example then processes signals derived from the multiple electrode channels to mitigate local noise effects in extracting the heart beat parameters. The system 200 can, however, be configured to determine values of any other suitable cardiovascular parameter, for a user who is performing any other suitable activity.

Embodiments, variations, and examples of the system 200 can implement components described in one or more of: U.S. application Ser. No. 14/541,446, entitled "System and Method for Monitoring Biometric Signals" and filed on 14 Nov. 2014, U.S. application Ser. No. 14/079,629, entitled "Wearable Architecture and Methods for Performance Monitoring, Analysis, and Feedback" and filed on 13 Nov. 2013, U.S. application Ser. No. 14/079,621, entitled "Wearable Performance Monitoring, Analysis, and Feedback Systems and Methods" and filed on 30 Jan. 2014, U.S. application Ser. No. 14/699,730, entitled "Biometric Electrode System and Method of Manufacture" and filed on 29 Apr. 2015, and U.S. application Ser. No. 14/742,420, entitled "Biometric Signal Conduction System and Method of Manufacture" and filed on 17 Jun. 2015, each of which is incorporated herein in its entirety by this reference. However, the system 200 can additionally or alternatively include any other suitable components.

2.1 System—Garment

The garment 205 is configured to be worn by the user at a first body region. The garment 205 functions to provide an article that can be worn by the user, wherein the sensor module 210 and/or the supplemental sensor module 220 can be removably integrated and/or configured for wireless communication of signals from integrated electrode systems and be worn by the user. The garment 205 can include one or more of: shorts, pants, tops, accessories (e.g., belts), and/or any other article of clothing. The first body region can include any one or more of: the gluteus maximus muscles, the gluteus medius muscles, the vastus lateralis muscles, the gracilis muscles, the semimembranosus muscles, the semitendinosis muscles, the biceps femoris, the soleus muscles, the gastrocnemius muscles, the rectus femoris muscles, the sartorius muscles, the peroneus longus muscles, the adductor longus muscles, and or any other suitable body region. In some variations, the system 200 can implement electrode systems integrated into garments (e.g., shorts, pants, tops, accessories (e.g. a belt)) 205 of the user, wherein the sensor module 210 and/or the supplemental sensor module 220 can be removably integrated and/or configured for wireless communication of signals; however, the system 200 can alternatively implement electrode systems that are not configured to be integrated into garments 205. The system 200 is preferably configured to implement at least a portion of the method 100 described in Section 1 above; however, the system 200 can alternatively implement any other suitable method.

The garment 205 can also include embodiments, variations, and examples described in one or more of: U.S. application Ser. No. 14/541,446, entitled "System and Method for Monitoring Biometric Signals" and filed on 14 Nov. 2014, U.S. application Ser. No. 14/079,629, entitled "Wearable Architecture and Methods for Performance Monitoring, Analysis, and Feedback" and filed on 13 Nov. 2013, U.S. application Ser. No. 14/079,621, entitled "Wearable Performance Monitoring, Analysis, and Feedback Systems and Methods" and filed on 30 Jan. 2014, U.S. application Ser. No. 14/699,730, entitled "Biometric Electrode System and Method of Manufacture" and filed on 29 Apr. 2015, and U.S. application Ser. No. 14/742,420, entitled "Biometric Signal Conduction System and Method of Manufacture" and filed on 17 Jun. 2015, each of which is herein incorporated in its entirety by this reference.

2.2 System—Sensor Module

Figure 16:
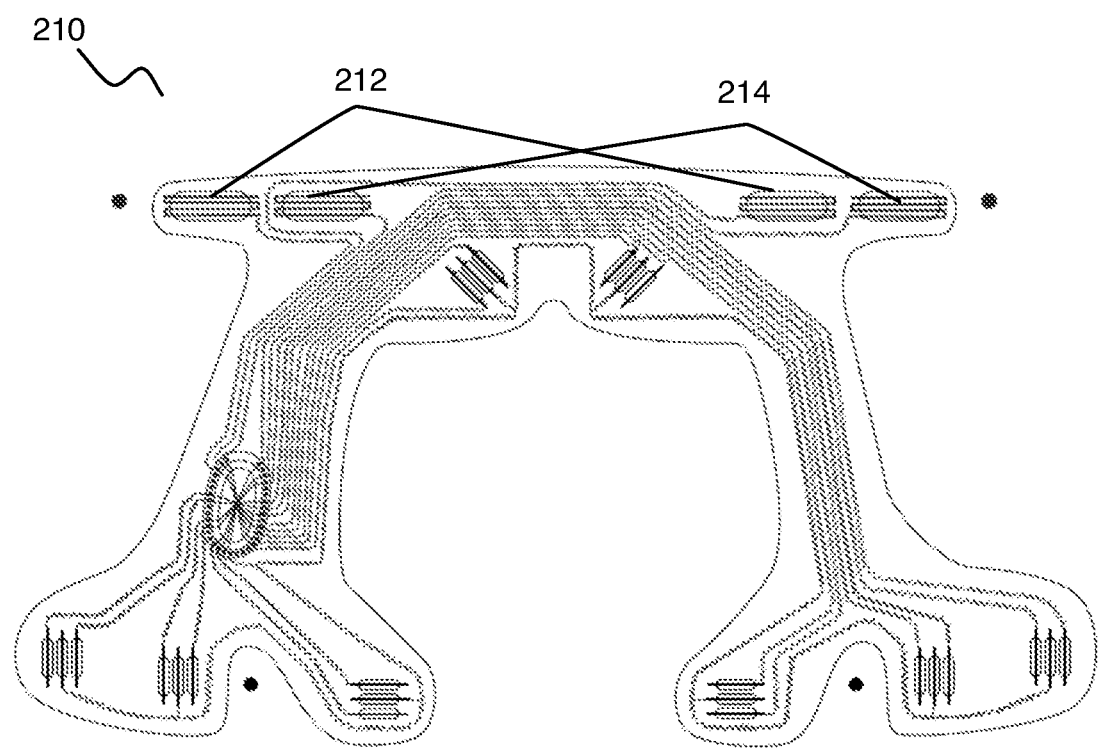
FIG. 16 depicts a specific embodiment of an electrode module in an embodiment of a system for communicating beat parameters to a user.

As shown in FIG. 16, the sensor module 210 includes a first unit comprising a first pair of electrodes 212 coupled to the user and a second unit comprising a second pair of electrodes 214 coupled to the user. The first unit can be associated with a first sensor channel 216 and the second unit can be associated with a second sensor channel 218, wherein the first channel can generate a first dataset and the second channel can generate a second dataset, each dataset based on generating bioelectrical signals from the heart of the user. The sensor module 210 functions to generate datasets based on detected bioelectrical signals derived from activity of the user's heart, in order to enable extraction of beat parameters during activity of the user. As such, each sensor channel 216, 218 can be derived from a consolidation of two electrode signals (e.g., a difference of two electrode signals); however, in alternative variations of the sensor module 210, each unit can include any suitable number of electrodes. The sensor module preferably generates a first and second dataset that include a heart signal component and a local noise component, but can additionally or alternatively include any other signal or noise component. In variations of a unit involving a pair of electrodes, the pair of electrodes is preferably positioned such that the electrodes oppose each other within the same plane (e.g., transverse plane) of the user's body. As such, a first vector (or projection thereof onto a plane) between electrodes 212 of a first unit and a second vector (or projection thereof onto the plane) between electrodes 214 of a second unit can cross, as shown in FIG. 2A, or may not cross, as shown in FIG. 2B.

Furthermore, all electrodes of units of the sensor module 210 preferably lie substantially within the same plane (e.g., a transverse plane through the user's body), such that vectors between the electrodes and a reference point (e.g., the user's heart) are approximately equal in magnitude. Such a configuration produces a high degree of correspondence between signals generated at the electrodes of the units. In variations, the plane can be a transverse plane through the user's body, at or below the umbilical region of the user (to provide a suitable distance from the heart of the user, in relation to signal timing) and at or above a plane through the greater trochanter bones of the user's femurs (in order to limit noise due to motion of the user). In one example, all electrodes can be positioned about the waistline of a garment (e.g., pants, shorts) 205 of the user. Alternatively, electrodes of different units corresponding to the sensor channels 216, 218 can lie within different planes (e.g., slightly offset planes), such that differences in magnitudes between vectors from the electrodes to a reference point (e.g., the user's heart) are negligible. Even further, all electrodes of units corresponding to sensor channels can be positioned such that they receive signals generated from the user's heart or any other suitable reference point with substantially the same timing. However, electrodes of units corresponding to the sensor channels can alternatively be positioned at any other suitable location, as shown in FIGS. 15A-15D, and subsequent blocks of the method 100 can be configured to account for distance and/or asymmetry in electrode configuration in extracting beat parameters from the datasets.

While two sensor channels 216, 218, each corresponding to a unit of two electrodes 212, 214, are described above, variations of the sensor module 210 can be expanded to include less than or more than two units with associated sensor channels (e.g., N sensor channels). For instance, in some variations, three sensor channels, each having a unit of two electrodes, can be used to generate three datasets for processing at the processing subsystem 234. In an example, as shown in FIGS. 3 and 16, electrodes of each unit can be positioned about the user's waistline and be located substantially within the same transverse plane through the user's body, in order to generate data which can be processed to identify beat parameters of the user.

Electrodes of the sensor module 210 and the supplemental sensor module 220 can include electrodes bonded or otherwise coupled to material of a wearable garment (e.g., shorts, pants), and can include any suitable features that facilitate signal acquisition and/or noise mitigation. For instance, an electrode can include any one or more of: a reference shield composed of a conductive material for static dissipation and electrical coupling to the user; a combination of biosensing contacts and reference contacts to facilitate contact with the user (e.g., without the use of a coupling medium), non-conductive housings with apertures configured to isolate exposed coupling regions; and any other suitable features.

The electrodes and biosensing contacts can additionally or alternatively include embodiments, variations, or examples as described in U.S. application Ser. No. 14/079,629 filed on 13 Nov. 2013 and entitled "Wearable Architecture and Methods for Performance Monitoring, Analysis, and Feedback", and U.S. application Ser. No. 14/699,730, entitled "Biometric Electrode System and Method of Manufacture" and filed on 29 Apr. 2015, each of which is herein incorporated in its entirety by this reference; however, the electrodes and biosensing contacts of the sensor module 210 can alternatively include any other suitable electrodes.

2.3 System—Supplemental Sensor Module

Figures 15A, 15B:
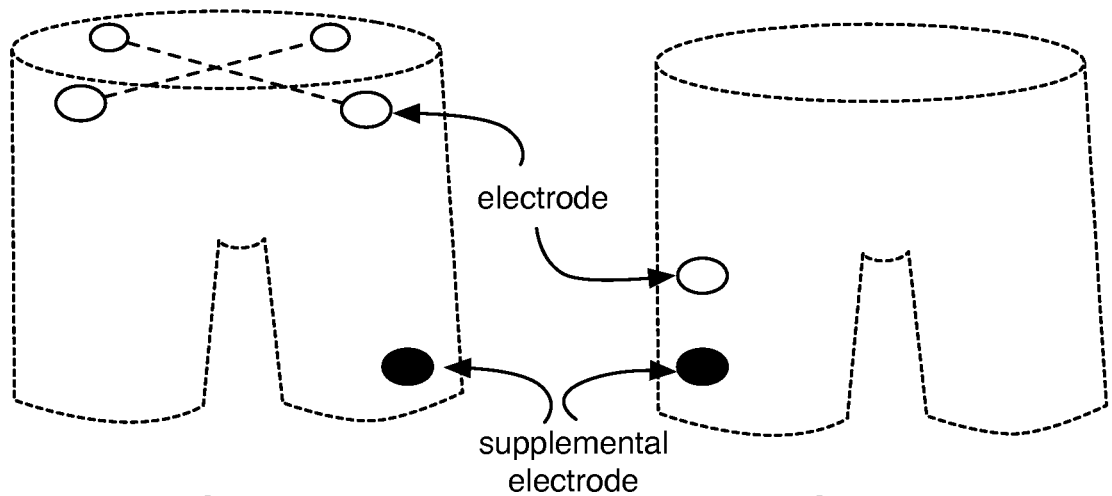
FIGS. 15A-15D depict variations of electrode module configurations in an embodiment of a system for communicating beat parameters to a user.
Figures 15C, 15D:
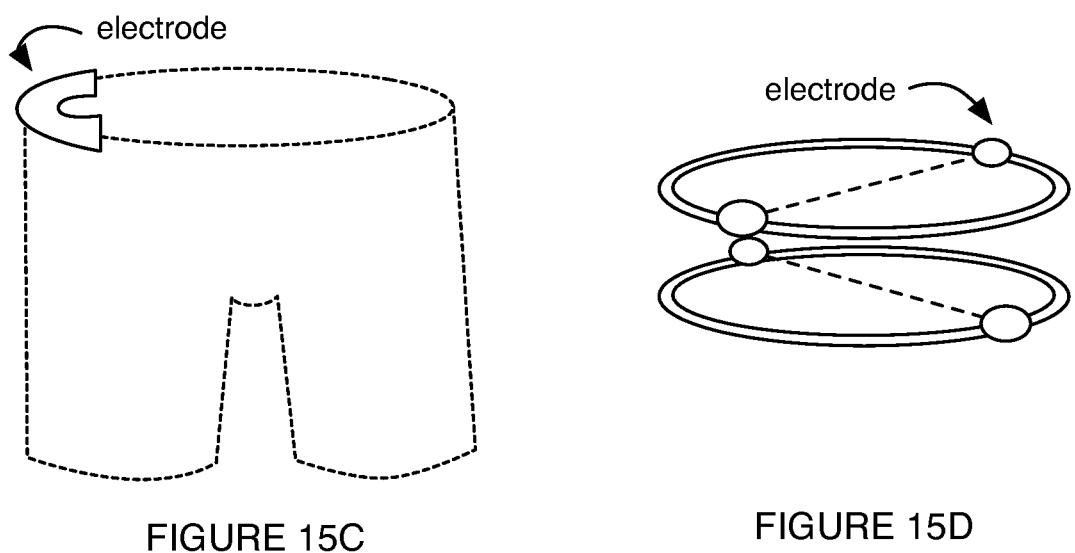

The supplemental sensor module 220 is configured to generate a supplemental dataset based on supplemental signals. The supplemental sensor module 220 functions to generate a supplemental dataset based on detected supplemental signals, in order to facilitate the isolation and separation of noise (e.g. locally-induced noise) from signals of interest. As shown in FIGS. 15A and 15B, the supplemental sensor module 220 is preferably coupled to the garment (e.g., shorts, pants, tops, accessories (e.g., belts), etc.) but can alternatively or additionally be coupled to a supplemental garment (e.g., a separate pair of shorts, pants, tops, accessories (e.g., belts)). In some variations, the vector between the first electrode pair 212, the vector between the second electrode pair 214, and the vectors between electrodes of the supplemental sensor module 220 can be positioned in a particular orientation (e.g., parallel, crossed, forming a square, etc.). Alternatively or additionally, the electrodes of the sensor module 210 and the electrodes of the supplemental sensor module 220 can lie substantially within the same plane (e.g., a transverse plane through the user). However, the electrodes of the supplemental sensor module 220 can be oriented and/or positioned with respect to the user and/or the electrodes of the sensor module 210 in any suitable manner.

The electrodes and biosensing contacts can additionally or alternatively include embodiments, variations, or examples as described in U.S. application Ser. No. 14/079,629 filed on 13 Nov. 2013 and entitled "Wearable Architecture and Methods for Performance Monitoring, Analysis, and Feedback", and U.S. application Ser. No. 14/699,730, entitled "Biometric Electrode System and Method of Manufacture" and filed on 29 Apr. 2015, each of which is herein incorporated in its entirety by this reference; however, the electrodes and biosensing contacts of the sensor module 210 can alternatively include any other suitable electrodes.

2.4 System—Control Module

The control module 230 includes a communication subsystem 232 in communication with the sensor module 210 and the supplemental sensor module 220; and a processing subsystem 234 in communication with the communication subsystem 232, and configured to: generate a combined dataset based upon a combination of the first dataset and the second dataset, calculate 1) a heart signal power spectrum based on the combined data set, and 2) a supplemental power spectrum based on the supplemental dataset, generate a noise-mitigated power spectrum based on processing the heart signal power spectrum with the supplemental power spectrum, generate an analysis of a beat parameter based upon the frequency parameter with highest power, and generate information to be rendered to the user at the user interface, wherein the information is derived from the beat parameter analysis. The control module functions to facilitate communication between system 200 components and to generate a beat parameter analysis upon which information can be derived to be rendered to the user at the user interface. The communication subsystem 232 functions to facilitate communication between system 200 components, and the processing subsystem 230 functions to implement at least a portion of the method 100 described in Section 1 above, but can alternatively be configured to implement any other suitable method. The communication subsystem 232 can preferably receive datasets from the sensor module 210 and/or supplemental sensor module 220, and transmit the datasets to the processing subsystem 234. In one application, the communication subsystem 232 can be implemented in a machine configured to interface directly with the sensor module 210 and/or supplemental sensor module 220 (e.g., using a wired or a wireless connection, using a connection through a garment integrated with the electrode module 205) to receive signals from the sensor module 210 and/or supplemental sensor module 220, and transfer data derived from the signals to a cloud-based computing system configured to perform a majority of an embodiment of the method 100 described above. However, the communication subsystem 232 can facilitate communication between the system 200 components in any other suitable manner. The subsystems of the control module 230 can alternatively be distributed across machine and cloud-based computing systems in any other suitable manner. The processing subsystem 230, as shown in FIG. 14, is preferably implemented in one or more computing systems, wherein the computing system(s) can be implemented at least in part in the cloud and/or as a machine (e.g., computing machine, server, etc.) configured to receive a computer-readable medium storing computer-readable instructions.

The control module 230, the communication subsystem 232, and the processing subsystem 234 can include any of the embodiments, variations, and examples described in one or more of: U.S. application Ser. No. 14/541,446, entitled "System and Method for Monitoring Biometric Signals" and filed on 14 Nov. 2014; and U.S. application Ser. No. 14/702,129, entitled "System and Method for Monitoring Biometric Signals" and filed on 14 Nov. 2014, each of which is herein incorporated in its entirety by this reference.

Variations of the method 100 and system 200 include any combination or permutation of the described components and processes. Furthermore, various processes of the preferred method can be embodied and/or implemented at least in part as a machine configured to receive a computer-readable medium storing computer-readable instructions. The instructions are preferably executed by computer-executable components preferably integrated with a system and one or more portions of the control module 155 and/or a processor. The computer-readable medium can be stored on any suitable computer readable media such as RAMs, ROMs, flash memory, EEPROMs, optical devices (CD or DVD), hard drives, floppy drives, or any suitable device. The computer-executable component is preferably a general or application specific processor, but any suitable dedicated hardware device or hardware/firmware combination device can additionally or alternatively execute the instructions.

The FIGURES illustrate the architecture, functionality and operation of possible implementations of systems, methods and computer program products according to preferred embodiments, example configurations, and variations thereof. In this regard, each block in the flowchart or block diagrams may represent a module, segment, step, or portion of code, which comprises one or more executable instructions for implementing the specified logical function(s). It should also be noted that, in some alternative implementations, the functions noted in the block can occur out of the order noted in the FIGURES. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

As a person skilled in the art will recognize from the previous detailed description and from the figures and claims, modifications and changes can be made to the preferred embodiments of the invention without departing from the scope of this invention defined in the following claims.

We claim:

1. A method for measuring heart beat parameters of a user with a frequency domain-based approach, the method comprising:
   receiving, at a processing subsystem in communication with an electrode module coupled to a garment worn by the user and comprising a first electrode pair associated with a first sensor channel and a second electrode pair associated with a second sensor channel, 1) a first dataset based on a first set of signals detected from the first sensor channel, and 2) a second dataset based on a second set of signals detected from the second sensor channel, wherein the first dataset and the second dataset comprise a local noise component and a heart signal component, the garment configured to abut a first body region located inferior to a L1 lumbar vertebrae region of a user;
   receiving, at the processing subsystem, an electromyography (EMG) dataset based on a set of EMG signals detected from an EMG sensor module coupled to the garment;
   generating noise-mitigated power spectrum by:
   calculating a combined EMG power spectrum based on combining a plurality of EMG power spectra calculated from the EMG dataset,
   generating a combined dataset based upon non-linearly combining the first and second datasets, wherein the combined dataset comprises a dampened local noise component and an accentuated heart signal component,
   after generating the combined dataset, calculating a heart power spectrum based on a sample of the combined data set, the sample having a time interval including signal components for a plurality of heart beats, wherein calculating the heart power spectrum comprises generating a power spectral density from a non-linear combination of multiple heart power spectra including the heart power spectrum, and
      after calculating the heart power spectrum, generating the noise-mitigated power spectrum at least in part by dividing the heart power spectrum by the combined EMG power spectrum, wherein generating the noise-mitigated power spectrum further comprises smoothing power spike features in the noise-mitigated power spectrum upon applying a moving average operation to the noise-mitigated power spectrum;
   generating a beat parameter analysis based upon the noise-mitigated power spectrum in the frequency domain;
   and
   rendering information derived from the beat parameter analysis on a user interface of an electronic device associated with the user.

2. The method of claim 1, wherein generating the noise-mitigated power spectrum comprises combining a power spectrum component corresponding to a harmonic frequency of the heart signal with a power spectrum component corresponding to a fundamental frequency of the heart signal.

3. The method of claim 1, wherein generating the noise-mitigated power spectrum comprises combining a power spectrum component corresponding to a harmonic frequency of the combined EMG power spectrum with a power spectrum component corresponding to a fundamental frequency of the combined EMG power spectrum.

4. The method of claim 1, further comprising identifying a frequency parameter with highest power in the noise-mitigated power spectrum, and wherein generating the beat parameter analysis comprises generating the beat parameter analysis based upon the frequency parameter with the highest power.

5. The method of claim 1, wherein generating the beat parameter analysis comprises:
   determining a set of heart rate components, wherein the set of heart rate components is associated with a set of time intervals in a one-to-one manner; and
   calculating a heart rate variability based on the set of heart rate components.

6. A system for measuring heart beat parameters of a user with a frequency domain-based approach, the system comprising:
   a garment configured to abut a first body region located inferior to a L1 lumbar vertebrae region of the user;
   a heart signal sensor module coupled to the garment and comprising:
      a first electrode pair and a second electrode pair oriented such that a first vector between electrodes of the first electrode pair and a second vector between electrodes of the second electrode pair are substantially crossed,
      a first sensor channel associated with the first electrode pair, and configured to generate a first dataset based on a first set of detected signals, and
      a second sensor channel associated with the second electrode pair, and configured to generate a second dataset based on a second set of detected signals, wherein the first dataset and the second dataset comprise a local noise component and a heart signal component;
   an electromyography (EMG) sensor module coupled to the garment, and configured to generate an EMG dataset based on a set of EMG signals detected by the EMG sensor module; and
   a control module comprising:
   a communication subsystem in communication with the heart signal sensor module and the EMG sensor module; and
   a processing subsystem in communication with the communication subsystem, and configured to:
   calculate a combined EMG power spectrum based on combining a plurality of EMG power spectra calculated from the EMG dataset;
   generate a combined dataset based upon non-linearly combining the first and second datasets, wherein the combined dataset comprises a dampened local noise component and an accentuated heart signal component,
   after generating the combined dataset, calculate a heart power spectrum based on a sample of the combined data set, the sample having a time interval including signal components for a plurality of heart beats, wherein calculating the heart power spectrum comprises generating a power spectral density from a non-linear combination of multiple heart power spectra including the heart power spectrum, and, after calculating the heart power spectrum, generate a noise-mitigated power spectrum at least in part by dividing the heart power spectrum by the combined EMG power spectrum, wherein generating the noise-mitigated power spectrum further comprises smoothing power spike features in the noise-mitigated power spectrum upon applying a moving average operation to the noise-mitigated power spectrum, generate an analysis of a beat parameter based upon the noise-mitigated power spectrum in the frequency domain, and generate information to be rendered on a user interface of an electronic device associated with the user, wherein the information is derived from the beat parameter analysis.

7. The system of claim 6, wherein the EMG sensor module interfaces with the user at a second body region located substantially proximal to at least one of a group of muscles comprising: a gluteus maximus muscle, a vastus lateralis muscle, a bicep femoris muscle, and a triceps surae muscle.

8. The system of claim 6, wherein the processing subsystem is further configured to identify a frequency parameter with highest power in the noise-mitigated power spectrum, and wherein the beat parameter analysis is generated based on the frequency parameter with the highest power.

9. The system of claim 6, wherein generating the noise-mitigated power spectrum comprises combining a power spectrum component corresponding to a harmonic frequency of the heart signal with a power spectrum component corresponding to a fundamental frequency of the heart signal.

10. The system of claim 6, wherein generating the noise-mitigated power spectrum comprises combining a power spectrum component corresponding to a harmonic frequency of the combined EMG power spectrum with a power spectrum component corresponding to the fundamental frequency of the combined EMG power spectrum.

11. The system of claim 6, wherein generating the beat parameter analysis comprises:
determining a set of heart rate components, wherein the set of heart rate components is associated with a set of time intervals in a one-to-one manner; and
calculating a heart rate variability based on the set of heart rate components.

12. The method of claim 1, wherein generating the combined dataset comprises:
identifying a noise removed subspace substantially orthogonal to the heart signal component based on a correlation between the first dataset and the second dataset; and
extracting the noise removed subspace from the combined dataset.

13. The method of claim 1, wherein generating the beat parameter analysis comprises predicting a confidence parameter indicating an accuracy level of the beat parameter analysis, based on running a predictive model trained on features predictive of the accuracy level, and wherein rendering information derived from the beat parameter analysis comprises:
comparing the confidence parameter to a threshold condition; and
in response to the confidence parameter satisfying the threshold condition, rendering information derived from the beat parameter analysis.

14. A method for measuring heart beat parameters of a user with a frequency domain-based approach, the method comprising:
receiving, at a processing subsystem in communication with an electrode module coupled to a garment worn by the user and comprising a first electrode pair associated with a first sensor channel and a second electrode pair associated with a second sensor channel, 1) a first dataset based on a first set of signals detected from the first sensor channel, and 2) a second dataset based on a second set of signals detected from the second sensor channel, wherein the first dataset and the second dataset comprise a local noise component and a heart signal component, the garment configured to abut a first body region located inferior to a L1 lumbar vertebrae region of a user;
receiving, at the processing subsystem, an electromyography (EMG) dataset based on a set of EMG signals detected from an EMG sensor module coupled to the garment;
generating a noise-mitigated power spectrum by:
calculating a combined EMG power spectrum based on combining a plurality of EMG power spectra calculated from the EMG dataset;
generating a combined dataset based upon non-linearly combining the first and second datasets, wherein the combined dataset comprises a dampened local noise component and an accentuated heart signal component;
after generating the combined dataset, calculating a heart power spectrum based on a sample of the combined data set, the sample having a time interval including signal components for a plurality of heart beats, wherein calculating the heart power spectrum comprises generating a power spectral density from a non-linear combination of multiple heart power spectra including the heart power spectrum, and;
after calculating the heart power spectrum, generating the noise-mitigated power spectrum by:
identifying a frequency range of the combined EMG power spectrum; and
filtering a portion of the heart power spectrum corresponding to the identified frequency range to produce the noise-mitigated power spectrum, wherein generating the noise-mitigated power spectrum further comprises smoothing power spike features in the noise-mitigated power spectrum upon applying a moving average operation to the noise-mitigated power spectrum;
generating a beat parameter analysis based upon the noise-mitigated power spectrum in the frequency domain;
and
rendering information derived from the beat parameter analysis on a user interface of an electronic device associated with the user.

15. The method of claim 14, wherein the identified frequency range of the combined EMG power spectrum corresponds to a local power maximum of the combined EMG power spectrum.

16. The method of claim 14, wherein generating the noise-mitigated power spectrum comprises combining a power spectrum component corresponding to a harmonic frequency of the heart signal with a power spectrum component corresponding to a fundamental frequency of the heart signal.

17. The method of claim 14, wherein generating the noise-mitigated power spectrum comprises combining a power spectrum component corresponding to a harmonic frequency of the combined EMG power spectrum with a power spectrum component corresponding to a fundamental frequency of the combined EMG power spectrum.

18. The method of claim 14, wherein rendering information derived from the beat parameter analysis comprises sending a notification indicative of a cardiovascular health condition of the user.

19. The method of claim 14, wherein generating the noise-mitigated power spectrum further comprises filtering signals associated with an estimate heart rate less than 54 beats per minute.

20. The method of claim 14, wherein generating the noise-mitigated power spectrum further comprises filtering signals associated with a sampling rate less than a lower sampling rate threshold or greater than a higher sampling rate threshold.

21. The method of claim 1, wherein applying the exponential moving average operation comprises applying a function with the form:

$$EMA_k = \gamma * EMA_{k-1} + 1 - \gamma * x[k]$$

where $EMA_k$ is an exponential moving average at a time period k, coefficient $\gamma$ is the degree of weighting decrease, and x[k] represents signal value during time period k.

22. The method of claim 1, wherein generating the combined dataset based upon non-linearly combining the first and second datasets comprises applying a combination function with the following form (where x is a first signal from the first dataset and y is a second signal from the second dataset): $f{x,y} = x*y1 + |x-y|$.

* * * * *